(12) United States Patent
Schlachter et al.

(10) Patent No.: US 10,368,930 B2
(45) Date of Patent: *Aug. 6, 2019

(54) MILLED BONE GRAFT MATERIALS AND METHODS OF USE

(71) Applicant: Warsaw Orthopedic, Inc., Warsaw, IN (US)

(72) Inventors: Kelly W. Schlachter, Mason, TN (US); Daniel A. Shimko, Germantown, TN (US); Kerem Kalpakci, Memphis, TN (US); Erick Vasquez, Memphis, TN (US); David R. Kaes, Toms River, NJ (US); Subhabrata Bhattacharyya, Metuchen, NJ (US)

(73) Assignee: Warsaw Orthopedic,Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/912,038

(22) Filed: Mar. 5, 2018

(65) Prior Publication Data

US 2018/0193077 A1 Jul. 12, 2018

Related U.S. Application Data

(62) Division of application No. 14/941,033, filed on Nov. 13, 2015, now Pat. No. 9,913,676.

(Continued)

(51) Int. Cl.
*A61B 17/88* (2006.01)
*A61F 2/28* (2006.01)
(Continued)

(52) U.S. Cl.
CPC ...... *A61B 17/8816* (2013.01); *A61B 17/8805* (2013.01); *A61F 2/28* (2013.01);
(Continued)

(58) Field of Classification Search
CPC .. A61F 2/28; A61F 2/46; A61F 2/4644; A61F 2/4601; A61F 2/30942;
(Continued)

(56) References Cited

U.S. PATENT DOCUMENTS 6,200,347 B1 * 3/2001 Anderson ................ A61F 2/28
623/16.11
6,458,375 B1 10/2002 Gertzman ................ A61F 2/28
424/422

(Continued)

OTHER PUBLICATIONS

International Preliminary Report on Patentability of the Patent Cooperation Treaty (PCT), International Bureau of WIPO, dated May 16, 2017 of International PCT Application No. PCT/US2015/060619 filed on Nov. 13, 2015.

(Continued)

*Primary Examiner* — Alvin J Stewart

(57) ABSTRACT

A bone material for hydration with a liquid is provided, the bone material comprising a coherent mass of milled and demineralized bone fibers, the coherent mass having no binder disposed in or on the coherent mass. In some embodiments, a bone material for hydration with a liquid is provided, the bone material comprising a coherent mass of cartridge milled, lyophilized and demineralized bone fibers, the coherent mass having no binder on the coherent mass. In some embodiments, a method of implanting a bone material is provided, the method comprising contacting the bone material with a liquid, the bone material comprising a coherent mass of cartridge milled, lyophilized and demineralized bone fibers, the coherent mass having no binder disposed in or on the coherent mass; molding the bone material into a shape to implant the bone material; and implanting the bone material at the target tissue site.

20 Claims, 18 Drawing Sheets

Related U.S. Application Data

(60) Provisional application No. 62/079,931, filed on Nov. 14, 2014, provisional application No. 62/079,916, filed on Nov. 14, 2014, provisional application No. 62/079,939, filed on Nov. 14, 2014.

(51) Int. Cl.
| | |
|---|---|
| *A61F 2/30* | (2006.01) |
| *A61L 27/36* | (2006.01) |
| *A61L 27/54* | (2006.01) |
| *B01F 13/00* | (2006.01) |
| *B01F 13/06* | (2006.01) |
| *B01F 15/00* | (2006.01) |
| *B01F 15/02* | (2006.01) |
| *A61F 2/46* | (2006.01) |

(52) U.S. Cl.
CPC ........ *A61F 2/30942* (2013.01); *A61F 2/4644* (2013.01); *A61L 27/365* (2013.01); *A61L 27/3608* (2013.01); *A61L 27/3683* (2013.01); *A61L 27/3691* (2013.01); *A61L 27/54* (2013.01); *B01F 13/0023* (2013.01); *B01F 13/06* (2013.01); *B01F 15/00506* (2013.01); *B01F 15/0278* (2013.01); *A61B 2017/8838* (2013.01); *A61F 2/4601* (2013.01); *A61F 2002/2835* (2013.01); *A61L 2300/412* (2013.01); *A61L 2430/02* (2013.01)

(58) Field of Classification Search
CPC ............... A61L 27/3608; A61L 27/365; A61L 27/3683; A61L 27/3691; A61L 27/54; A61B 17/8816; A61B 17/8805
See application file for complete search history.

(56) References Cited

U.S. PATENT DOCUMENTS

| | | | | |
|---|---|---|---|---|
| 6,468,311 B2* | 10/2002 | Boyd | A61F 2/28 | 623/17.11 |
| 6,569,201 B2* | 5/2003 | Moumene | A61F 2/447 | 606/247 |
| 6,696,073 B2* | 2/2004 | Boyce | A61B 17/0401 | 424/422 |
| 6,989,031 B2* | 1/2006 | Michelson | A61F 2/28 | 623/17.11 |
| 7,189,263 B2* | 3/2007 | Erbe | A61B 17/80 | 424/422 |
| 7,723,395 B2* | 5/2010 | Ringeisen | A61B 17/0642 | 521/50 |
| 7,763,072 B2* | 7/2010 | Bianchi | A61F 2/08 | 623/13.14 |
| 7,794,500 B2* | 9/2010 | Felix | A61F 2/447 | 606/246 |
| 7,901,457 B2* | 3/2011 | Truncale | A61F 2/28 | 623/16.11 |
| 7,938,857 B2* | 5/2011 | Garcia-Bengochea | A61B 17/1671 | 623/17.11 |
| 8,105,379 B2* | 1/2012 | Carter | A61B 17/1635 | 623/13.17 |
| 8,110,001 B2* | 2/2012 | Carter | A61B 17/1635 | 623/13.14 |
| 8,133,421 B2* | 3/2012 | Boyce | A61B 17/0401 | 264/109 |
| 8,389,588 B2* | 3/2013 | Ringeisen | A61B 17/80 | 424/422 |
| 9,289,312 B2* | 3/2016 | Davenport | A61L 27/042 | |
| 9,333,082 B2 | 5/2016 | Wei | A61K 35/32 | |
| 9,352,003 B1 | 5/2016 | Semler | A61K 35/32 | |
| 9,414,939 B2 | 8/2016 | Shimko | A61F 2/4601 | |
| 9,486,500 B2 | 11/2016 | McKay | A61F 2/28 | |
| 9,579,421 B2 | 2/2017 | Bhat | A61L 27/3821 | |
| 9,623,153 B2 | 4/2017 | McKay | A61L 27/24 | |
| 9,636,436 B2 | 5/2017 | Carter | A61L 27/3608 | |
| 9,744,052 B2* | 8/2017 | Moskowitz | A61F 2/447 | |
| 9,763,787 B2* | 9/2017 | Bianchi | A61L 2/025 | |
| 9,913,676 B2* | 3/2018 | Schlachter | A61F 2/28 | |
| 10,194,964 B2* | 2/2019 | Schlachter | A61F 2/28 | |
| 2003/0009235 A1* | 1/2003 | Manrique | A61B 17/866 | 623/23.63 |
| 2003/0143258 A1 | 7/2003 | Knaack | A61L 27/227 | 424/426 |
| 2004/0023387 A1 | 2/2004 | Morris | A61F 2/4644 | 435/379 |
| 2004/0249463 A1 | 12/2004 | Bindseil | A61F 2/28 | 623/17.16 |
| 2004/0249464 A1 | 12/2004 | Bindseil | A61F 2/4455 | 623/17.16 |
| 2005/0059953 A1 | 3/2005 | Gaskins | A61L 27/3683 | 604/500 |
| 2005/0149173 A1 | 7/2005 | Hunter | A61B 17/12022 | 623/1.42 |
| 2005/0186240 A1 | 8/2005 | Ringeisen et al. | | |
| 2005/0283255 A1 | 12/2005 | Geremakis | A61F 2/4644 | 623/23.51 |
| 2006/0083769 A1 | 4/2006 | Kumar et al. | | |
| 2007/0082057 A1 | 4/2007 | Masinaei | A61K 35/32 | 424/549 |
| 2007/0207186 A1 | 9/2007 | Scanlon | A61F 2/07 | 424/424 |
| 2007/0269481 A1 | 11/2007 | Li | A61L 27/18 | 424/423 |
| 2008/0063671 A1 | 3/2008 | Morris | A61L 24/0005 | 424/400 |
| 2008/0262633 A1 | 10/2008 | Williams | A61L 27/3608 | 623/23.63 |
| 2008/0305145 A1 | 12/2008 | Shelby | A61F 2/4644 | 424/423 |
| 2009/0130173 A1 | 5/2009 | Behnam | A61L 27/3604 | 424/426 |
| 2009/0157087 A1 | 6/2009 | Wei | A61B 17/7097 | 606/99 |
| 2009/0220605 A1 | 9/2009 | Wei | A61F 2/28 | 424/486 |
| 2009/0226523 A1 | 9/2009 | Behnam | A61L 27/3608 | 424/488 |
| 2009/0319045 A1 | 12/2009 | Truncale | A61F 2/28 | 623/16.11 |
| 2010/0129415 A1 | 5/2010 | Kinnane | A61L 27/3604 | 424/423 |
| 2010/0268278 A1 | 10/2010 | Foley | A61B 17/7059 | 606/263 |
| 2010/0292791 A1 | 11/2010 | Lu | A61K 38/18 | 623/13.12 |
| 2010/0297082 A1 | 11/2010 | Guelcher | A61K 31/00 | 424/93.1 |
| 2010/0303881 A1 | 12/2010 | Hoke | A61K 9/70 | 424/423 |
| 2011/0009960 A1 | 1/2011 | Altman | A61F 2/0059 | 623/8 |
| 2011/0054408 A1 | 3/2011 | Wei | A61B 17/68 | 604/175 |
| 2011/0070312 A1 | 3/2011 | Wei | A61L 27/3608 | 424/549 |
| 2012/0009230 A1 | 1/2012 | Drapeau | A61L 27/20 | 424/400 |
| 2012/0041444 A1 | 2/2012 | Einhorn | A61L 24/0094 | 606/92 |
| 2012/0071884 A1 | 3/2012 | Cooper et al. | | |
| 2013/0115457 A1 | 5/2013 | Haynie | D01D 5/003 | 428/401 |
| 2013/0190891 A1 | 7/2013 | Drapeau | A61F 2/28 | 623/23.58 |
| 2013/0195805 A1 | 8/2013 | Wei | A61K 35/28 | 424/93.7 |
| 2013/0261634 A1 | 10/2013 | McKay | A61F 2/2846 | 606/93 |

(56) References Cited

U.S. PATENT DOCUMENTS

| | | | |
|---|---|---|---|
| 2014/0005793 A1 | 1/2014 | Koford | A61L 27/50 623/23.5 |
| 2014/0081414 A1 | 3/2014 | Hall | A61L 27/16 623/23.7 |
| 2014/0205674 A1 | 7/2014 | Wei | A61K 35/28 424/549 |
| 2014/0208980 A1 | 7/2014 | Song | A61L 27/3608 106/124.7 |
| 2014/0212471 A1 | 7/2014 | Drapeau | A61K 35/32 424/443 |
| 2014/0271785 A1 | 9/2014 | Bagga | A61L 27/56 424/443 |
| 2014/0314822 A1 | 10/2014 | Carter et al. | |
| 2015/0010607 A1 | 1/2015 | Francis | A61K 35/28 424/422 |
| 2015/0093574 A1 | 4/2015 | Tayi | D01F 6/68 428/401 |
| 2015/0112287 A1 | 4/2015 | Bowlin | A61L 15/28 604/304 |
| 2015/0238318 A1 | 8/2015 | McCullen | A61F 2/30756 623/14.12 |
| 2015/0251361 A1 | 9/2015 | Meyer | B29C 67/24 428/332 |
| 2015/0306278 A1 | 10/2015 | McKay | A61L 27/3608 424/444 |
| 2015/0374450 A1 | 12/2015 | Mansfield | A61L 27/3604 264/219 |
| 2016/0000062 A1 | 1/2016 | Chen | A61M 5/002 435/1.3 |
| 2016/0022146 A1 | 1/2016 | Piron | A61B 90/39 600/411 |
| 2016/0067375 A1 | 3/2016 | Holmes | A61L 27/18 623/23.58 |
| 2016/0106838 A1 | 4/2016 | D'Agostino | A61B 17/7233 623/23.51 |
| 2016/0135954 A1 | 5/2016 | Schlachter | A61F 2/28 623/23.63 |
| 2016/0174777 A1 | 6/2016 | Wang | A47K 10/16 442/57 |
| 2016/0361171 A1 | 12/2016 | Wang | A61L 27/3608 |
| 2016/0361467 A1 | 12/2016 | Klimek | A61F 2/28 |
| 2017/0072089 A1 | 3/2017 | Nseir Manassa | B32B 7/02 |
| 2017/0216491 A1* | 8/2017 | Schlachter | A61L 2/087 |
| 2017/0281829 A1 | 10/2017 | Biris | A61L 27/58 |
| 2017/0296581 A1 | 10/2017 | Behnam | A61L 27/3604 |

OTHER PUBLICATIONS

Written Opinion of the International Searching Authority (ISA/US) dated Mar. 11, 2016 of International PCT Application No. PCT/US2015/060619 filed on Nov. 13, 2015.

International Search Report of the International Searching Authority (ISA/US) dated Mar. 11, 2016 of International PCT Application No. PCT/US2015/060619 filed on Nov. 13, 2015.

* cited by examiner

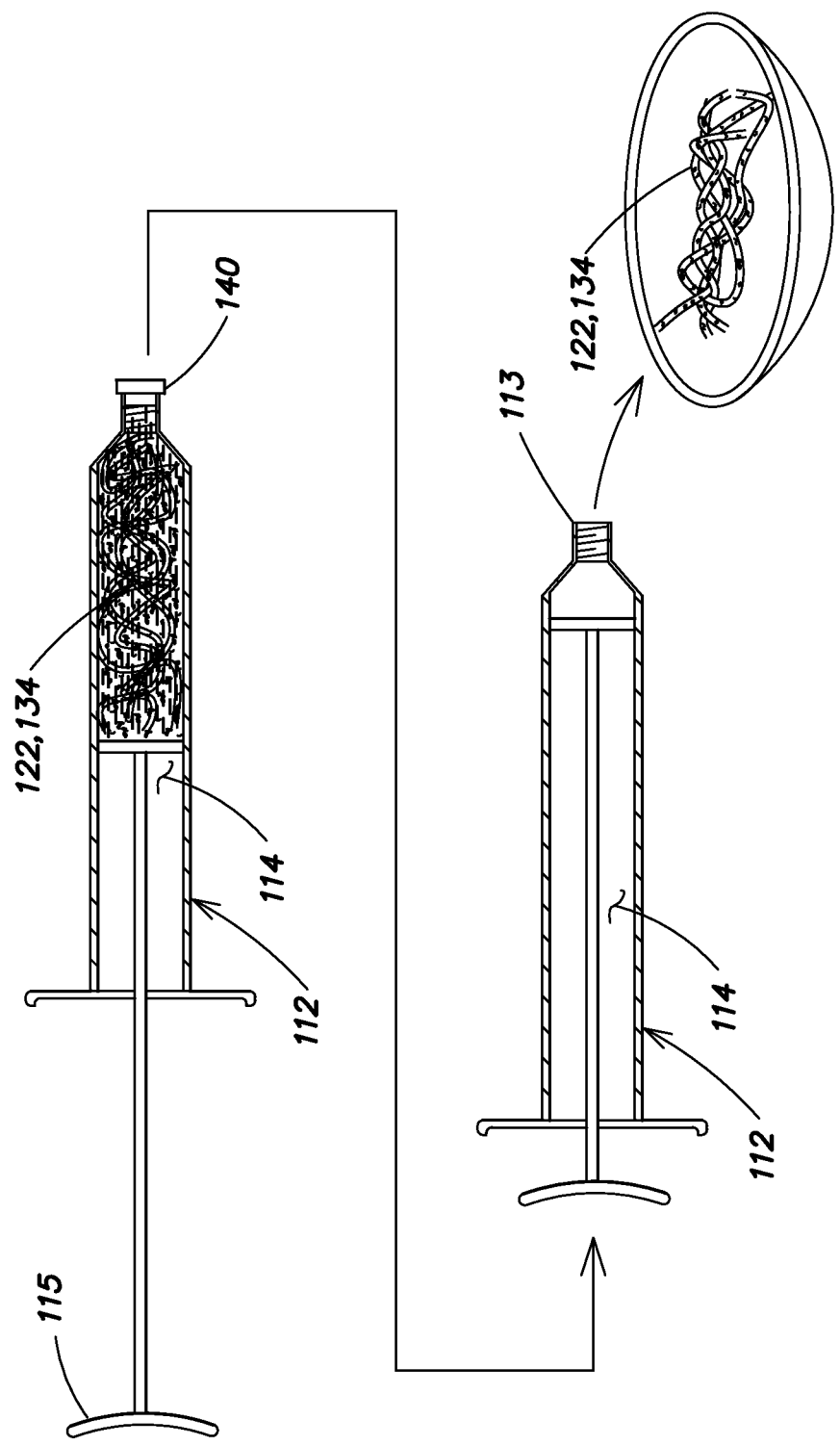

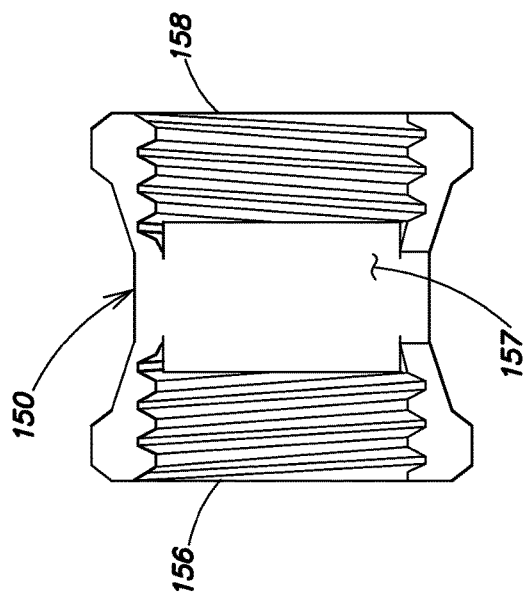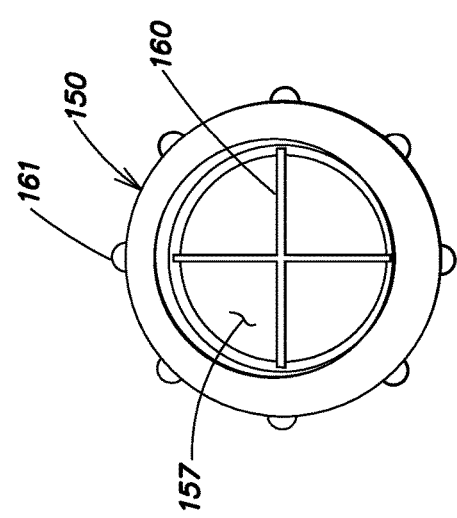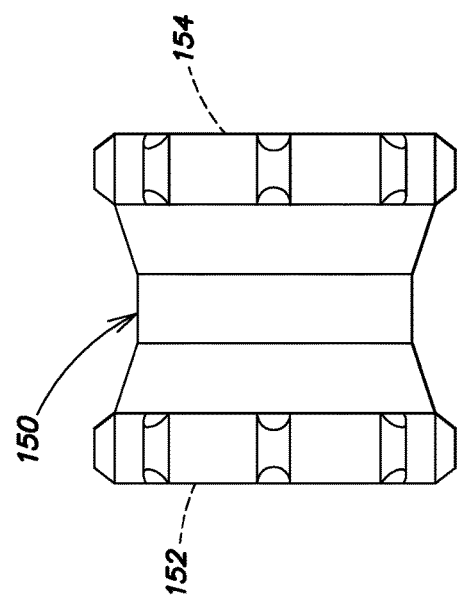

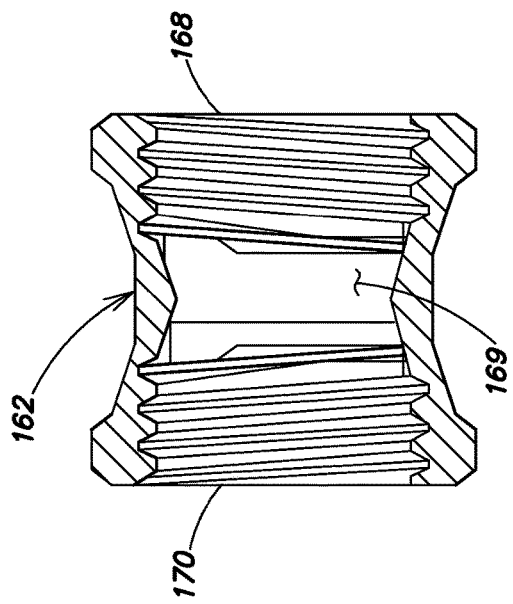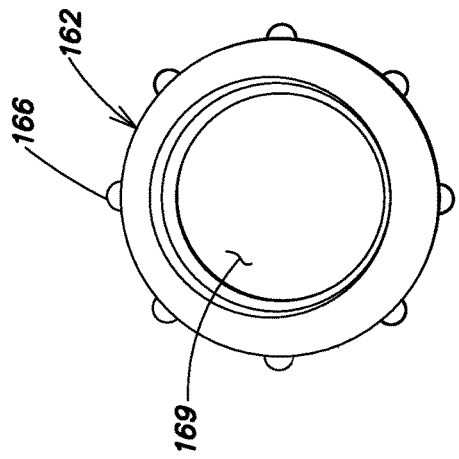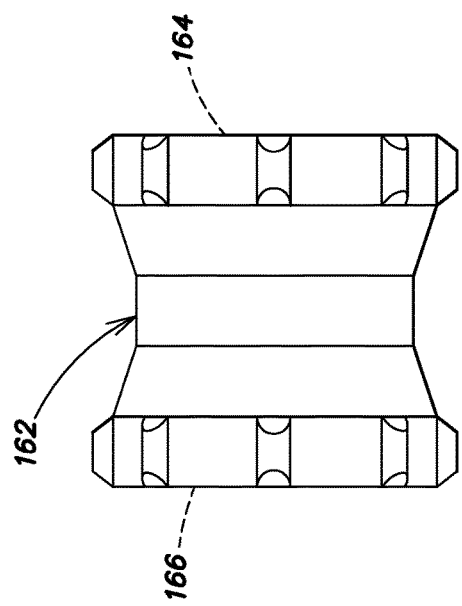

MILLED BONE GRAFT MATERIALS AND METHODS OF USE

This application claims the benefit of the filing date of U.S. Provisional Application No. 62/079,916, filed Nov. 14, 2014, entitled "SHAPED BONE GRAFT MATERIALS AND METHODS OF USE"; U.S. Provisional Application No. 62/079,931, filed Nov. 14, 2014, entitled "MILLED BONE GRAFT MATERIALS AND METHODS OF USE"; and 62/079,939, filed Nov. 14, 2014, entitled "BONE GRAFT MATERIALS, DEVICES AND METHODS OF USE". These entire disclosures are hereby incorporated by reference into the present disclosure.

BACKGROUND

It is estimated that more than half a million bone grafting procedures are performed in the United States annually with a cost over $2.5 billion. These numbers are expected to double by 2020. Both natural bone and bone substitutes have been used as graft materials. Natural bone may be autograft or allograft. Bone substitutes include natural or synthetic materials such as collagen, silicone, acrylics, calcium phosphate, calcium sulfate, or the like.

There are at least three ways in which a bone graft can help repair a defect. The first is osteogenesis, the formation of new bone within the graft by the presence of bone-forming cells called osteoprogenitor cells. The second is osteoinduction, a process in which molecules contained within the graft (e.g., bone morphogenic proteins and other growth factors) convert progenitor cells into bone-forming cells. The third is osteoconduction, a physical effect by which a matrix often containing graft material acts as a scaffold on which bone and cells in the recipient are able to form. The scaffolds promote the migration, proliferation and differentiation of bone cells for bone regeneration.

Demineralized bone matrix (DBM) has been shown to exhibit the ability to induce and/or conduct the formation of bone. It is therefore desirable to implant and maintain demineralized bone matrix at a site which bone growth is desired.

Bone fiber based-demineralized bone matrices for implantation exhibit improvements in mechanical properties, including cohesiveness, fiber length, fiber diameter or width, fiber aspect ratio, or a combination of multiple variables.

Oftentimes, when DBM fibers are made they lack cohesiveness and tend to fall apart or become loose in the package or during processing. In order to reduce this tendency, a binder (e.g., glycerol) is commonly added to keep the DBM fibers together. The inclusion of a binder can lead to additional manufacturing expenses and further complicate regulatory approval processes.

Therefore, there is a need for DBM compositions, devices and methods that allow osteogenesis, osteoinduction and/or osteoconduction. DBM compositions, devices and methods that can be made from bone material that does not need a binder would be beneficial. Furthermore, DBM compositions, devices and methods that easily allow hydration of the demineralized bone matrix would be beneficial.

SUMMARY

DBM compositions, devices and methods are provided that allow osteogenesis, osteoinduction and/or osteoconduction. The DBM compositions, devices and methods provided, in some embodiments, are made from bone material that does not contain a binder. DBM compositions, devices and methods that easily allow hydration of the demineralized bone matrix are also provided.

In some embodiments, compositions and methods are provided for a bone material for hydration with a liquid, the bone material comprising a coherent mass of milled and demineralized bone fibers, the coherent mass of demineralized fiber having no binder disposed in or on the coherent mass.

In some embodiments, compositions and methods are provided for a bone material for hydration with a liquid, the bone material comprising a coherent mass of cartridge milled, lyophilized and demineralized bone fibers, the coherent mass of demineralized fiber having no binder disposed in or on the coherent mass.

In some embodiments, a method for implanting a bone material to a target tissue site is provided. The method comprises contacting the bone material with a liquid, the bone material comprising a coherent mass of cartridge milled, lyophilized and demineralized bone fibers, the coherent mass of demineralized fiber having no binder disposed in or on the coherent mass; molding the bone material into a shape to implant the bone material; and implanting the bone material at the target tissue site.

In some embodiments, a device for mixing a bone material with a liquid is provided. The device comprises a chamber having a proximal end and a distal end, and the bone material disposed within the chamber, the bone material comprising a coherent mass of milled and lyophilized demineralized bone fibers; and a plunger having at least a portion slidably disposed within the proximal end of the chamber and configured to dispense the bone material mixed with liquid from the distal end of the chamber, when the plunger is in an extended position.

In some embodiments, a device for mixing a bone material with a liquid is provided. The device comprises a first chamber having a proximal end and a distal end, and the bone material disposed within the first chamber, the bone material comprising a coherent mass of milled and lyophilized demineralized bone fibers; and a first plunger having at least a portion slidably disposed within the proximal end of the first chamber; a second chamber having a proximal end and a distal end, and a liquid disposed within the second chamber, the liquid configured to hydrate the coherent mass of milled and lyophilized demineralized bone fibers; and a second plunger having at least a portion slidably disposed within the proximal end of the second chamber; a connector fluidly coupling the distal end of the first chamber to the distal end of the second chamber, wherein movement of the second plunger to an extended position causes liquid to flow to hydrate the coherent mass of milled and lyophilized demineralized bone fibers in the first chamber.

In some embodiments, a method for hydrating a bone material with a liquid is provided. The method comprises mixing the liquid with the bone material comprising a coherent mass of milled and lyophilized demineralized bone fibers in a device comprising a first chamber having a proximal end and a distal end, and the bone material disposed within the first chamber; and a first plunger having at least a portion slidably disposed within the proximal end of the first chamber; a second chamber having a proximal end and a distal end, and the liquid disposed within the second chamber, the liquid configured to hydrate the coherent mass of milled and lyophilized demineralized bone fibers; and a second plunger having at least a portion slidably disposed within the proximal end of the second chamber; a connector fluidly coupling the distal end of the first chamber to the distal end of the second chamber, wherein movement of the second plunger to an extended position causes liquid to flow to hydrate the coherent mass of milled and lyophilized demineralized bone fibers in the first chamber.

In some embodiments, compositions and methods are provided for a bone material comprising a coherent mass of cartridge milled and demineralized bone fibers, the coherent mass of cartridge milled and demineralized bone fibers having no binder disposed in or on the coherent mass.

In some embodiments, compositions and methods are provided for a bone material comprising a coherent mass of cartridge milled and demineralized bone fibers, the coherent mass of cartridge milled and demineralized bone fibers having no binder disposed in or on the coherent mass.

In some embodiments, a method of making an implantable bone material is provided. The method comprises drying a coherent mass of cartridge milled and demineralized bone fibers, the coherent mass of cartridge milled and demineralized bone fibers having no binder disposed in or on the coherent mass Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 17 depicts the first syringe of the mixing device of FIG. 14. The first syringe is removed from the connector. The hydrated bone material is encased in the first chamber of the first syringe. A cap attached to an end of the chamber is removed and the hydrated bone material is ejected or extruded from the first chamber of the first syringe. Depending on the degree of hydration, the hydrated bone material becomes a moldable putty that can be injected or implanted into a surgical site.

FIG. 18A illustrates a perspective view of the connector that can engage the first and second syringe.

FIG. 18B illustrates a cross-sectional view of the connector having threading that can engage the first and second syringe.

FIG. 18C illustrates a side perspective view of the connector having channels that can engage the first syringe.

FIG. 19A illustrates a perspective view of the connector that can engage the first and second syringe.

FIG. 19B illustrates a cross-sectional view of the connector having threading that can engage the first and second syringe.

FIG. 19C illustrates a side perspective view of the connector having a channel and threading that can engage the first or second syringe.

Figure 1:
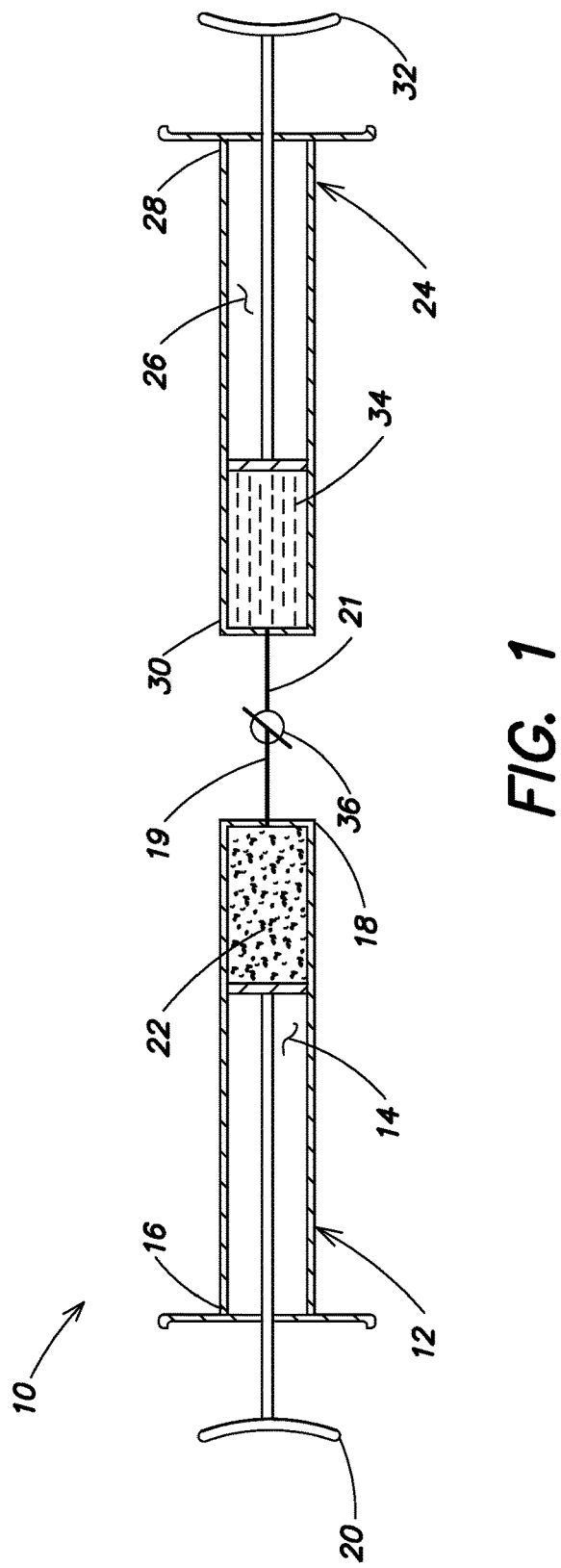
FIG. 1 depicts a mixing device for mixing a bone material with a liquid. The mixing device comprises a first syringe and a second syringe. The first syringe comprises a bone material comprising a coherent mass of milled and lyophilized demineralized bone fibers. The second syringe comprises a liquid. The syringes are connected via a connector.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of promoting an understanding of the principles of the disclosure, reference will now be made to certain embodiments and specific language will be used to describe the same. It will nevertheless be understood that no limitation of the scope of the disclosure is thereby intended, such alterations and further modifications in the illustrated device, and such further applications of the principles of the disclosure as described herein being contemplated as would normally occur to one skilled in the art to which the disclosure relates.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical representations are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this disclosure belongs.

Unless explicitly stated or apparent from context, the following terms are phrases have the definitions provided below:

Definitions

It is noted that, as used in this specification and the appended claims, the singular forms "a," "an," and "the," include plural referents unless expressly and unequivocally limited to one referent. Thus, for example, reference to "an allograft" includes one, two, three or more allografts.

The term "biodegradable" includes that all or parts of the carrier and/or implant will degrade over time by the action of enzymes, by hydrolytic action and/or by other similar mechanisms in the human body. In various embodiments, "biodegradable" includes that the carrier and/or implant can break down or degrade within the body to non-toxic components after or while a therapeutic agent has been or is being released. By "bioerodible" it is meant that the carrier and/or implant will erode or degrade over time due, at least in part, to contact with substances found in the surrounding tissue, fluids or by cellular action.

The term "mammal" refers to organisms from the taxonomy class "mammalian," including but not limited to humans, other primates such as chimpanzees, apes, orangutans and monkeys, rats, mice, cats, dogs, cows, horses, etc.

A "therapeutically effective amount" or "effective amount" is such that when administered, the drug (e.g., growth factor) results in alteration of the biological activity, such as, for example, promotion of bone, cartilage and/or other tissue (e.g., vascular tissue) growth, inhibition of inflammation, reduction or alleviation of pain, improvement in the condition through inhibition of an immunologic response, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the implant is designed for immediate release. In other embodiments the implant is designed for sustained release. In other embodiments, the implant comprises one or more immediate release surfaces and one or more sustained release surfaces.

The terms "treating" and "treatment" when used in connection with a disease or condition refer to executing a protocol that may include a bone repair procedure, where the bone implant and/or one or more drugs are administered to a patient (human, other normal or otherwise or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient.

The term "bone," as used herein, refers to bone that is cortical, cancellous or cortico-cancellous of autogenous, allogeneic, xenogeneic, or transgenic origin.

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "osteoconductive," as used herein, refers to the ability of a non-osteoinductive substance to serve as a suitable template or substance along which bone may grow.

The term "osteoinductive," as used herein, refers to the quality of being able to recruit cells from the host that have the potential to stimulate new bone formation. Any material that can induce the formation of ectopic bone in the soft tissue of an animal is considered osteoinductive.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

The term "osteogenic" refers to the ability of a graft material to produce bone independently. To have direct osteogenic activity, the graft must contain cellular components that directly induce bone formation. For example, an allograft seeded with activated MSCs would have the potential to induce bone formation directly, without recruitment and activation of host MSC populations. Because many osteoconductive allografts also have the ability to bind and deliver bioactive molecules, their osteoinductive potential will be greatly enhanced.

The term "osteoimplant," as used herein, refers to any bone-derived implant prepared in accordance with the embodiments of this disclosure and, therefore, is intended to include expressions such as bone membrane or bone graft.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "demineralized," as used herein, refers to any material generated by removing mineral material from tissue, e.g., bone tissue. In certain embodiments, the demineralized compositions described herein include preparations containing less than 5%, 4%, 3%, 2% or 1% calcium by weight. Partially demineralized bone (e.g., preparations with greater than 5% calcium by weight but containing less than 100% of the original starting amount of calcium) is also considered within the scope of the disclosure. In some embodiments, partially demineralized bone contains preparations with greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of the original starting amount of calcium. In some embodiments, demineralized bone has less than 95% of its original mineral content. In some embodiments, demineralized bone has less than 95%, 90%, 85%, 80%, 75%, 70%, 65%, 60%, 55%, 50%, 45%, 40%, 35%, 30%, 25%, 20%, 15%, 10%, or 5% of its original mineral content. Demineralized is intended to encompass such expressions as "substantially demineralized," "partially demineralized," and "fully demineralized." In some embodiments, part or all of the surface of the bone can be demineralized. For example, part or all of the surface of the allograft can be demineralized to a depth of from about 100 to about 5000 microns, or about 150 microns to about 1000 microns. In some embodiments, part or all of the surface of the allograft can be demineralized to a depth of from about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950 to about 5000 microns. If desired, the outer surface of the intervertebral implant can be masked with an acid resistant coating or otherwise treated to selectively demineralize unmasked portions of the outer surface of the intervertebral implant so that the surface demineralization is at discrete positions on the implant.

The term "demineralized bone matrix," as used herein, refers to any material generated by removing mineral material from bone tissue. In some embodiments, the DBM compositions as used herein include preparations containing less than 5%, 4%, 3%, 2% or 1% calcium by weight.

The term "superficially demineralized," as used herein, refers to bone-derived elements possessing at least about 90, 91, 92, 93, 94, 95, 96, 97, 98 or 99 weight percent of their original inorganic mineral content. The expression "partially demineralized" as used herein refers to bone-derived elements possessing from about 8 to about 90 weight percent of their original inorganic mineral content. In some embodiments, partially demineralized refers to bone-derived elements possessing from about 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88 to about 90 weight percent of their original inorganic mineral content. The expression "fully demineralized" as used herein refers to bone containing less than 8%, 7%, 6%, 5%, 4%, 3%, 2%, or 1% of its original mineral context.

The terms "pulverized bone", "powdered bone" or "bone powder" as used herein, refers to bone particles of a wide range of average particle size ranging from relatively fine powders to coarse grains and even larger chips.

The allograft can comprise bone fibers. Fibers include bone elements whose average length to average thickness ratio or aspect ratio of the fiber is from about 50:1 to about 1000:1. In overall appearance the fibrous bone elements can be described as elongated bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the elongated bone fibers are of irregular shapes including, for example, linear, serpentine or curved shapes. The elongated bone fibers are preferably demineralized, however, some of the original mineral content may be retained when desirable for a particular embodiment. The fibers when wet relax because they are porous, as they dry, they become more entangled and form a coherent mass as the fibers interconnect. In some embodiments, even when the fibers are wet, they are still cohesive.

"Non-fibrous", as used herein, refers to elements that have an average width substantially smaller than the average thickness of the fibrous bone element or aspect ratio of less than from about 50:1 to about 1000:1. For example, allograft bone fibers will have a fiber shape, while the non-fibrous material will not have a fiber shape but will have a shape such as, for example, triangular prism, sphere, cube, cylinder, square, triangle, particle, powder, and other regular or irregular shapes.

"Pressed bone fibers", as used herein, refer to bone fibers formed by applying pressure to bone stock. The bone utilized as the starting, or stock, material may range in size from relatively small pieces of bone to bone of such dimensions as to be recognizable as to its anatomical origin. The bone may be substantially fully demineralized, surface demineralized, partially demineralized, or nondemineralized. In general, the pieces or sections of whole bone stock can range from about 1 to about 400 mm, from about 5 to about 100 mm, in median length, from about 0.5 to about 20 mm, or from about 2 to about 10 mm, in median thickness and from about 1 to about 20 mm, or from about 2 to about 10 mm, in median width. Forming bone fibers by pressing results in intact bone fibers of longer length than other methods of producing the elongate bone fibers retaining more of the native collagen structure. The bone fibers may be made via a cartridge mill.

"High porosity", as used herein refers to having a pore structure that is conducive to cell ingrowth, and the ability to promote cell adhesion, proliferation and differentiation.

"Resorbable", as used herein, refers to a material that exhibits chemical dissolution when placed in a mammalian body.

"Bioactive agent" or "bioactive compound", as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD.

"Coherent mass", as used herein, refers to a plurality of bone fibers, in some embodiments, bound to one another by mechanical interlocking properties of the fibers. The cohesive mass may be in a variety of shapes and sizes, and is implantable into a surgical location. The cohesive mass comprises at least two curled or partially curled bone fibers that entangle with one another to maintain a connection without the use of a binding agent or carrier. In some embodiments, the fibers when wet relax because they are porous, as they dry, they become more entangled and form a coherent mass as the fibers interconnect.

Reference will now be made in detail to certain embodiments of the disclosure. The disclosure is intended to cover all alternatives, modifications, and equivalents that may be included within the disclosure as defined by the appended claims.

The headings below are not meant to limit the disclosure in any way; embodiments under any one heading may be used in conjunction with embodiments under any other heading.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

Bone Material

DBM compositions and methods that allow osteogenesis, osteoinduction and/or osteoconduction are provided. DBM compositions, devices and methods are provided that allow osteogenesis, osteoinduction and/or osteoconduction. The DBM compositions, devices and methods provided, in some embodiments, are made from bone material that does not contain a binder. DBM compositions, devices and methods that easily allow hydration of the demineralized bone matrix are also provided.

Compositions and methods are provided for a bone material for hydration with a liquid, the bone material comprising a coherent mass of milled and demineralized bone fibers, the coherent mass of demineralized fiber having no binder disposed in or on the coherent mass. In some embodiments, the bone material is lyophilized. In some embodiments, the demineralized bone fibers are cartridge milled and have a ribbon-like shape and increased surface area. In some embodiments, the coherent mass of milled and lyophilized demineralized bone fibers are cartridge milled fibers having a ribbon-like shape, increased surface area and a curled portion. In some embodiments, the coherent mass of milled and lyophilized demineralized bone fibers comprises autograft or allograft bone. In some embodiments, the bone fibers have a diameter from about 100 µm to about 2 mm. In some embodiments, the bone fibers have a length from about 0.5 mm to about 50 mm. In some embodiments, the bone fibers have an average length from about 0.5 cm to about 10 cm. In some embodiments, the fibers have an aspect ratio of from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1. In some embodiments, the liquid for hydration of the fibers comprises blood, water, saline or a combination thereof. In some embodiments, the liquid for hydration of the fibers is mixed with the coherent mass of milled and demineralized bone fibers that are lyophilized without a binder to form moldable lyophilized demineralized bone fiber.

In some embodiments, the bone fibers have a ribbon like shape and have increased surface area by from about 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 55.0, 60.0, 65.0, 70.0, 75.0, 80.0, 85.0, 90.0, 95.0, to about 100.0% when compared to bone chips, or powders.

In some embodiments, a device for mixing a bone material with a liquid is provided. The device comprises a chamber having a proximal end and a distal end, and the bone material disposed within the chamber, the bone material comprising a coherent mass of milled and lyophilized demineralized bone fibers; and a plunger having at least a portion slidably disposed within the proximal end of the chamber and configured to dispense the bone material mixed with liquid from the distal end of the chamber, when the plunger is in an extended position. In some embodiments, the chamber comprises a syringe barrel. In some embodiments, the coherent mass of milled and lyophilized demineralized bone fibers does not contain a binder. In some embodiments, the coherent mass of milled and lyophilized demineralized bone fibers comprises cartridge milled fibers having a curled portion. In some embodiments, the coherent mass of milled and lyophilized demineralized bone fibers comprises autograft or allograft bone. In some embodiments, the bone fibers have a diameter from about 100 μm to about 2 mm. In some embodiments, the bone fibers have a length from about 0.5 mm to about 50 mm. In some embodiments, the bone fibers have an average length from about 0.5 cm to about 10 cm. In some embodiments, the fibers have an aspect ratio of from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1. In some embodiments, the liquid for hydration of the fibers comprises blood, water, saline or a combination thereof. In some embodiments, the liquid is mixed lyophilized demineralized bone fibers to form moldable lyophilized demineralized bone fiber. In some embodiments, the liquid is mixed with the lyophilized demineralized bone fibers using negative pressure created in the chamber by the plunger. In some embodiments, the distal end of the chamber comprises a removable cap.

In some embodiments, a method for hydrating a bone material with a liquid is provided. The method comprises mixing the liquid with the bone material comprising a coherent mass of milled and lyophilized demineralized bone fibers in a device comprising a first chamber having a proximal end and a distal end, and the bone material disposed within the first chamber; and a first plunger having at least a portion slidably disposed within the proximal end of the first chamber; a second chamber having a proximal end and a distal end, and the liquid disposed within the second chamber, the liquid configured to hydrate the coherent mass of milled and lyophilized demineralized bone fibers; and a second plunger having at least a portion slidably disposed within the proximal end of the second chamber; a connector fluidly coupling the distal end of the first chamber to the distal end of the second chamber, wherein movement of the second plunger to an extended position causes liquid to flow to hydrate the coherent mass of milled and lyophilized demineralized bone fibers in the first chamber.

Compositions and methods are provided for a bone material comprising a coherent mass of cartridge milled and demineralized bone fibers, the coherent mass of cartridge milled and demineralized bone fibers having no binder disposed in or on the coherent mass. In some embodiments, the bone material comprises cortical bone, cancellous bone, cortico-cancellous bone, or mixtures thereof. In some embodiments, the bone material is obtained from autogenous bone, allogeneic bone, xenogeneic bone, or mixtures thereof. In some embodiments, the coherent mass is lyophilized and shaped. In some embodiments, the shape of the lyophilized coherent mass is cube, square, triangle, rectangular, circular, disc or cylinder shape. In some embodiments, the shape of the lyophilized coherent mass is disc shaped and the disc has a reservoir configured to contact a liquid. In some embodiments, the shape of the lyophilized coherent mass is cylinder shaped. In some embodiments, the coherent mass has a plurality of channels running longitudinally through the center of the cylinder shaped bone material to allow fluid to hydrate the bone material. In some embodiments, the coherent mass has a plurality of channels running longitudinally through the exterior of the cylinder shaped bone material to allow fluid to hydrate the bone material. In some embodiments, the cylinder shaped bone material further comprises a plurality of channels running longitudinally through an exterior of the bone material to allow fluid to hydrate the bone material.

Compositions and methods are provided for an implantable bone graft comprising fibers obtained from allograft bone, the fibers comprising hooking portions configured to interlock with one another to form a coherent mass, wherein the composition does not include a binding agent.

Typically, when bone is processed into particles or fibers, it is statically charged and not coherent or adherent. The processed bone is normally contained within an external structure (i.e., a bag or covering) or mixed with a carrier or binding agent to provide a cohesive structure. When implanted, this external structure or carrier must be removed by the patient's body, potentially impacting the osteoinductive potential of the graft.

In some embodiments, a cohesive mass of bone fibers without additional carrier contains bone processed in such a way that it provides for cohesion between fibers without additional containment or binding agents is provided. Bone shafts are milled to create curled bone fibers which are subsequently demineralized and freeze-dried. The fiber shape is altered during the drying process, which leads to physical entanglement and surface to surface interactions between adjacent fibers. The entanglement/interaction of the fibers is responsible for the cohesiveness of the final product. Thus, the present disclosure provides for a fibrous bone material having a size and shape that provides for increased surface area and the ability to mechanically interlock with one another to form an implantable coherent mass.

The compositions of the present disclosure results are utilized in an effective bone grafting product. The bone graft material is resorbed/remodeled and replaced by host bone during the healing process. In some embodiments, the bone material disclosed herein includes additional additives, such as synthetic ceramics and/or bioerodible polymers, which produce high concentrations of calcium, phosphate and silicon ions that act as a nidus for de-novo bone formation, as discussed herein. As the bioerodible polymer degrades faster than the ceramic, more and more osteoinductive DBM particles are exposed. The slower resorbing ceramic may act as a solid surface for stem cells and osteoblasts to attach to and begin laying down new bone.

The coherent mass of the disclosure has good flexibility and is compression resistant. It is also osteoinductive with the demineralized bone matrix retaining activity. These properties make an excellent bone graft substitute in that it may not break, crack, or deform when implanted in the body.

The implantable composition may be a combination of fibers of bone matrix from allograft bone and fibers of non-allograft bone material. The fibers of the non-allograft bone material comprise non-fibrous demineralized bone matrix particles embedded within or dispersed on the fibers of the non-allograft bone material. The ratio of fibers of demineralized bone matrix from allograft material to fibers of non-allograft material ranges from about 20:80 to about 70:30. In one embodiment, the ratio of fibers from allograft material to fibers of non-allograft material ranges from about 40:60 to about 60:40. In one embodiment, the ratio of fibers of demineralized bone matrix from allograft material to fibers of non-allograft material is about 50:50.

In some embodiments, the demineralized bone material includes particles that are non-fibrous. In some embodiments, the particles are powders, microspheres, sponges, pastes, gels, and/or granules. In one embodiment, the particles are powders.

In some embodiments, the demineralized bone material fibers comprise from about 1 to about 70 micrometers or from about 125 to about 250 micrometers. In some embodiments, the demineralized bone material fibers comprise about 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248 and/or 250 micrometers. In some embodiments, the bone fibers include a length from about 100 micrometers to about 2 mm. In some embodiments, the bone fibers have a length from about 0.5 cm to about 10 cm, about 1 cm to about 8 cm, about 3 cm to about 5 cm, about 0.5 mm to about 50 mm, about 1.0 mm to about 25 mm, or about 5 mm to about 10 mm. The fibers include a diameter of about 100 micrometers to about 2 mm.

The fibers are milled in such a way as to provide increased surface area in a compact shape and size. In some embodiments, the fibers include a curled shape such that diameter of the curled fibers is between about 50 micrometers and about 3 mm, and the diameter of the fibers in a flattened configuration is about 125 micrometers to about 5 mm. In some embodiments, the fibers include a curled shape such that diameter of the curled fibers is between about 100 micrometers and about 1 mm, and the diameter of the fibers in a flattened configuration is about 250 micrometers to about 2 mm.

In various embodiments, the fibers have an aspect ratio of length to width from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1. In other embodiments, the fibers have an aspect ratio of length to width of about 4:1, 17:1, or 23:1.

The composition has very low immunogenicity and good compatibility to fill a bone void.

DBM fibers for use in the present disclosure can be obtained commercially or can be prepared by known techniques. In general, advantageous, osteoinductive DBM materials can be prepared by decalcification of cortical and/or cancellous bone fibers, often by acid extraction. The fibers can be milled for example cartridge milled. The acid extraction process can be conducted so as to leave collagen, noncollagenous proteins, and growth factors together in a solid fiber. Methods for preparing bioactive demineralized bone are described in U.S. Pat. Nos. 5,073,373; 5,484,601; and 5,284,655, as examples. DBM products are also available commercially, including for instance, from sources such as Regeneration Technologies, Inc. (Alachua, Fla.), The American Red Cross (Arlington, Va.), and others. Bone fibers that are solely osteoconductive can be prepared using similar techniques that have been modified or supplemented to remove or inactivate (e.g. by crosslinking or otherwise denaturing) components in the bone matrix responsible for osteoinductivity. Osteoinductive and/or osteoconductive DBM materials used in the present disclosure can be derived from human donor tissue, especially in regard to implant devices intended for use in human subjects.

In regard to the fiber content of the coherent mass on a dry weight basis, the bone fiber material can constitute about 5% to about 100% of the compositions, about 20% to about 80%, or about 25% to about 75% by weight.

In some embodiments, the bone fibers of allograft bone have an average length to average thickness ratio or aspect ratio of the fibers from about 50:1 to about 1000:1. In overall appearance the bone fibers can be in the form of ribbons, threads, narrow strips, and/or thin sheets. The elongated bone fibers can be substantially linear in appearance or they can be coiled to resemble springs. In some embodiments, the bone fibers have linear portions and coiled portions. In some embodiments, the bone fibers are of irregular shapes including, for example, linear, serpentine and/or curved shapes. In some embodiments, the fibers can be curled at the edges to have a substantially hemicircular cross-sections. In some embodiments, the fibers may be entirely or partially helical, circumvoluted or in the shape of a corkscrew. The elongated bone fibers can be demineralized however some of the original mineral content may be retained when desirable for a particular embodiment. The bone graft fiber may further comprise mineralized bone material.

Figure 5:
FIG. 5 depicts mineralized fibers having increased surface area. The fibers are milled from bone shafts using any appropriate apparatus, such as a cartridge mill. The fibers are milled to include curled shapes having frayed portions and/or hooked portions to facilitate mechanical interlocking of the fibers.
Figure 6:
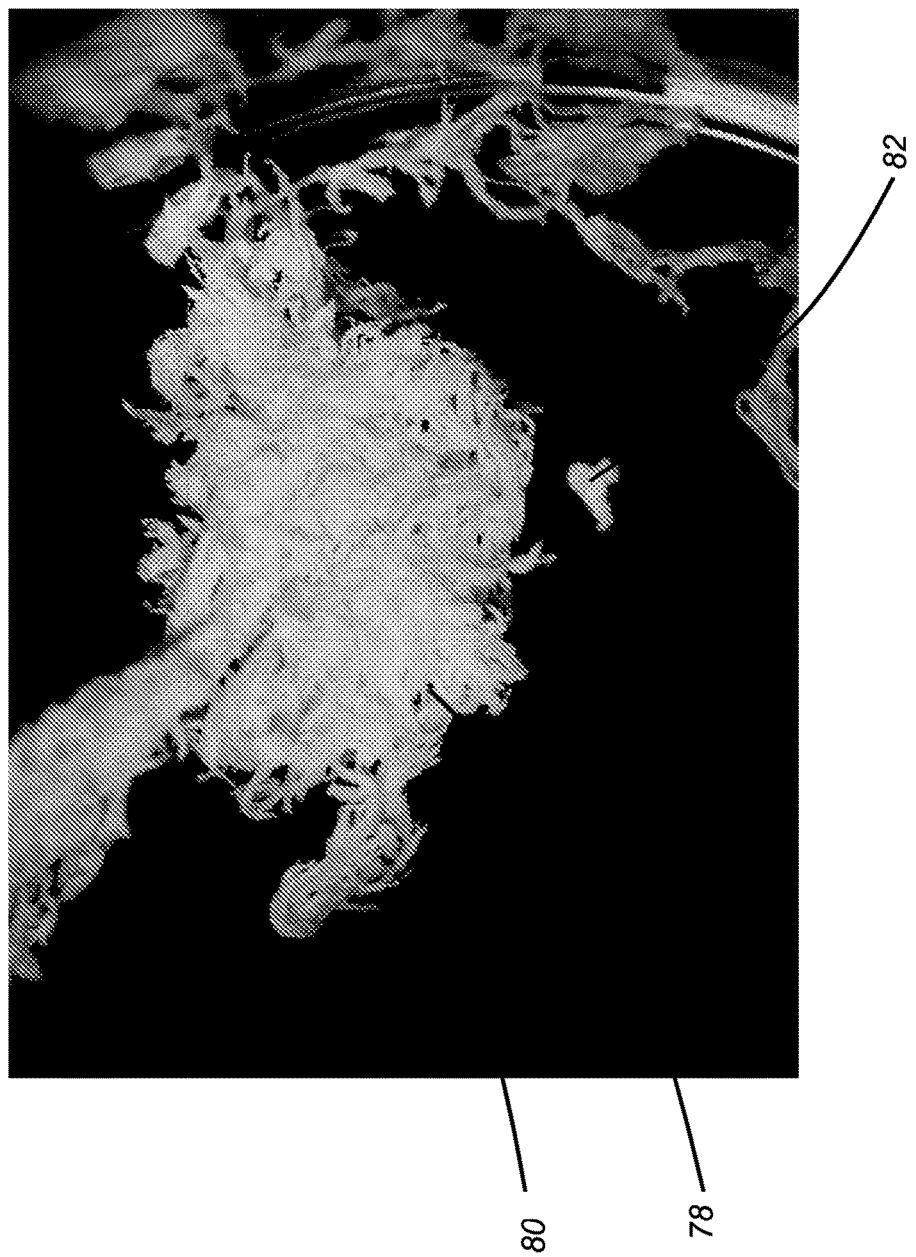
FIG. 6 depicts a bone material comprising a coherent mass of milled and lyophilized demineralized bone fibers. Lyophilization of the fibers alters the curls of the fibers to facilitate mechanical interlocking of the fibers. The lyophilized fibers form a coherent mass without the use of a binding agent or a carrier.

The bone fibers are elongated and curled to increase the surface area of the strips. The curled fibers may include frayed portions along the edges to facilitate interactions with other bone fibers. In some embodiments, the curled fibers are milled to have hooked portions along the edges of the fibers configured to engage with other fibers. Such frayed and hooked portions are illustrated, for example, in FIGS. 5 and 6. The hooked portions may engage other hooked portions, frayed portions, straightened portions or curled portions of other fibers. The hooked and frayed portions and the curled shape of the fibers provide for entanglement between fibers such that the fibers form a coherent mass without the need for a carrier or binding agent. For example, FIG. 5 illustrates bone fibers 74 produced from a cartridge mill. FIG. 6 illustrates a coherent mass of demineralized bone after it has been demineralized and contaminants remove by alcohol soaking, the wet fibers relax and entangle further after drying.

The bone fiber sizes and shapes may be created in a number of ways, for example, through cartridge milling. One such example of a suitable cartridge mill is the Osteobiologic Milling Machine, as described in U.S. Patent Publication No. 2012/0160945, assigned to Warsaw Orthopedic, Inc. and is hereby incorporated by reference in its entirety. However, it is contemplated that the bone fibers may be alternatively milled using vices, cutters, rollers, rotating rasps or reciprocating blade mills.

Non-Bone Material Additives

In some embodiments, the bone material may be combined with non-bone material additives after demineralization and/or lyophilization and before implantation. For example, the bone material may be combined with a bioerodible polymer. The bioerodible polymer exhibits dissolution when placed in a mammalian body and may be hydrophilic (e.g., collagen, hyaluronic acid, polyethylene glycol). Synthetic polymers are suitable according to the present disclosure, as they are biocompatible and available in a range of copolymer ratios to control their degradation.

In some embodiments, hydrophobic polymers (e.g. poly (lactide-co-glycolyde), polyanhydrides) may be used. Alternatively, a combination of hydrophilic and hydrophobic polymers may be used in the bone graft composition of the disclosure.

Exemplary materials may include biopolymers and synthetic polymers such as human skin, human hair, bone, collagen, fat, thin cross-linked sheets containing fibers and/or fibers and chips, polyethylene glycol (PEG), chitosan, alginate sheets, cellulose sheets, hyaluronic acid sheet, as well as copolymer blends of poly (lactide-co-glycolide) PLGA.

In some embodiments, the particles disclosed herein can also include other biocompatible and bioresorbable substances. These materials may include, for example, natural polymers such as proteins and polypeptides, glycosaminoglycans, proteoglycans, elastin, hyaluronic acid, dermatan sulfate, gelatin, or mixtures or composites thereof. Synthetic polymers may also be incorporated into the bone graft composites. These include, for example biodegradable synthetic polymers such as polylactic acid, polyglycolide, polylactic polyglycolic acid copolymers ("PLGA"), polycaprolactone ("PCL"), poly(dioxanone), poly(trimethylene carbonate) copolymers, polyglyconate, poly(propylene fumarate), poly(ethylene terephthalate), poly(butylene terephthalate), polyethylene glycol, polycaprolactone copolymers, polyhydroxybutyrate, polyhydroxyvalerate, tyrosine-derived polycarbonates and any random or (multi-) block copolymers, such as bipolymer, terpolymer, quaterpolymer, etc., that can be polymerized from the monomers related to previously-listed homo- and copolymers.

The bioerodible polymer may have a molecular weight of from about 1,000 to about 30,000 Daltons (Da). In various embodiments, the polymer may have a molecular weight of from about 2,000 to about 10,000 Da. In some embodiments, the polymer may have a molecular weight of from about 2,000 to 4,000 Da or from about 3,000 to 4,000 Da. In some embodiments, the bioerodible polymer may have a molecular weight of 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or about 30,000 Da.

In some embodiments, the bioerodible polymer is collagen. Collagen has excellent histocompatibility without antibody formation or graft rejection. Any suitable collagen material may be used, including known collagen materials, or collagen materials as disclosed in U.S. patent application Ser. No. 12/030,181, filed Feb. 12, 2008, hereby incorporated by reference in its entirety. Various collagen materials can be used, alone or in combination with other materials.

Insoluble collagen material for use in the disclosure can be derived from natural tissue sources, (e.g. xenogeneic, allogeneic, or autogenic relative to the recipient human or other patient) or recombinantly prepared. Collagens can be subclassified into several different types depending upon their amino acid sequence, carbohydrate content and the presence or absence of disulfide crosslinks. Types I and III collagen are two of the most common subtypes of collagen and may be used in the present disclosure. Type I collagen is present in skin, tendon and bone, whereas Type III collagen is found primarily in skin. The collagen used in compositions of the disclosure can be obtained from skin, bone, tendon, or cartilage and purified by methods well known in the art and industry. Alternatively, the collagen can be purchased from commercial sources.

The collagen can be atelopeptide collagen and/or telopeptide collagen. Still further, either or both of non-fibrillar and fibrillar collagen can be used. Non-fibrillar collagen is collagen that has been solubilized and has not been reconstituted into its native fibrillar form.

Suitable collagen products are available commercially, including for example from Kensey Nash Corporation (Exton, Pa.), which manufactures a fibrous collagen known as Semed F, from bovine hides. Collagen materials derived from bovine hide are also manufactured by Integra Life Science Holding Corporation (Plainsboro, N.J.). Naturally-derived or recombinant human collagen materials are also suitable for use in the disclosure. Illustratively, recombinant human collagen products are available from Fibrogen, Inc. (San Francisco, Calif.).

In some embodiments, the fibers can be combined with synthetic ceramics that are effective to provide a scaffold for bone growth and which are completely bioresorbable and biocompatible. The synthetic ceramics should provide high local concentrations of calcium, phosphate and silicon ions that act as a nidus for de-novo bone formation. The use of such a resorbable ceramics provides many advantages over alternative conventional materials. For instance, it eliminates the need for post-therapy surgery for removal and degrades in the human body to biocompatible, bioresorbable products.

In some embodiments, the synthetic ceramics disclosed herein may be selected from one or more materials comprising calcium phosphate ceramics or silicon ceramics. Biological glasses such as calcium-silicate-based bioglass, silicon calcium phosphate, tricalcium phosphate (TCP), biphasic calcium phosphate, calcium sulfate, hydroxyapatite, coralline hydroxyapatite, silicon carbide, silicon nitride ($Si_3N_4$), and biocompatible ceramics may be used. In some embodiments, the ceramic is tri-calcium phosphate or biphasic calcium phosphate and silicon ceramics. In some embodiments, the ceramic is tricalcium phosphate.

In some embodiments, the ceramics are a combination of a calcium phosphate ceramic and a silicon ceramic. In some embodiments, the calcium phosphate ceramic is resorbable biphasic calcium phosphate (BCP) or resorbable tri-calcium phosphate (TCP), most preferably resorbable TCP.

Biphasic calcium phosphate can have a tricalcium phosphate:hydroxyapatite weight ratio of about 50:50 to about 95:5, about 70:30 to about 95:5, about 80:20 to about 90:10, or about 85:15. The mineral material can be a granular particulate having an average particle diameter between about 0.2 and 5.0 mm, between about 0.4 and 3.0 mm, or between about 0.4 and 2.0 mm.

The ceramics of the disclosure may also be oxide ceramics such as alumina ($Al_2O_3$) or zirconia ($ZrO_2$) or composite combinations of oxides and non-oxides such as silicon nitride).

In some embodiments, after the coherent mass of DBM fibers is formed, a binding agent may be added to it before implantation. However, in some embodiments, the coherent mass of DBM fibers does not contain a binding agent and is stays together without the use of a binding agent. Examples of suitable binding agents that optionally can be included after the coherent mass is formed include, but are not limited to: (i) Polyhydroxy compound, for example, such classes of compounds as the acyclic polyhydric alcohols, non-reducing sugars, sugar alcohols, sugar acids, monosaccharides, disaccharides, water-soluble or water dispersible oligosaccarides, polysaccharides and known derivatives of the foregoing. Specific polyhydroxy compounds include, 1,2-propanediol, glycerol, 1,4,-butylene glycol trimethylolethane, trimethylolpropane, erythritol, pentaerythritol, ethylene glycols, diethylene glycol, triethylene glycol, tetraethylene glycol, propylene glycol, dipropylene glycol; polyoxyethylene-polyoxypropylene copolymer, for example, of the type known and commercially available under the trade names Pluronic and Emkalyx; polyoxyethylene-polyoxypropylene block copolymer, for example, of the type known and commercially available under the trade name Poloxamer; alkylphenolhydroxypolyoxyethylene, for example, of the type known and commercially available under the trade name Triton, polyoxyalkylene glycols such as the polyethylene glycols, xylitol, sorbitol, mannitol, dulcitol, arabinose, xylose, ribose, adonitol, arabitol, inositol, fructose, galactose, glucose, mannose, sorbose, sucrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose, mixtures of any of the foregoing.

The carrier or binding agent may further comprise a hydrogel such as hyaluronic acid, dextran, pluronic block copolymers of polyethylene oxide and polypropylene, and others. Suitable polyhodroxy compounds include such classes of compounds as acyclic polyhydric alcohols, non-reducing sugars, sugar alcohols, sugar acids, monosaccharides, disaccharides, water-soluble or water dispersible oligosaccharides, polysaccharides and known derivatives of the foregoing. An example carrier comprises glyceryl monolaurate dissolved in glycerol or a 4:1 to 1:4 weight mixture of glycerol and propylene glycol. Settable materials may be used, and they may set up either in situ, or prior to implantation. Optionally, xenogeneic bone powder carriers also may be treated with proteases such as trypsin. Xenogeneic carriers may be treated with one or more fibril modifying agents to increase the intraparticle intrusion volume (porosity) and surface area. Useful agents include solvents such as dichloromethane, trichloroacetic acid, acetonitrile and acids such as trifluoroacetic acid and hydrogen fluoride. The choice of carrier may depend on the desired characteristics of the composition. In some embodiments, a lubricant, such as water, glycerol, or polyethylene glycol may be added.

In some embodiments, the composition containing the fibers may also contain other beneficial substances including for example preservatives, cosolvents, suspending agents, viscosity enhancing agents, ionic strength and osmolality adjusters and/or other excipients. Suitable buffering agents can also be used an include but are not limited to alkaline earth metal carbonates, phosphates, bicarbonates, citrates, borates, acetates, succinates, or others. Illustrative-specific buffering agents include for instance sodium phosphate, sodium citrate, sodium borate, sodium acetate, sodium bicarbonate, sodium carbonate, and sodium tromethanine (TRIS).

In some embodiments, the cohesive mass of bone fibers may be mixed with a porogen material which is later removed during manufacturing to enhance porosity of the dried cohesive mass. Suitable porogen materials may be made of any biocompatible, biodegradable substance that can be formed into a particle and that is capable of at least substantially retaining its shape during the manufacturing of the implant, but is later removed or degrades or dissolves when placed in contact with an aqueous solution, or other liquid. The porogens, in some embodiments, may be inorganic or organic, for example, they may be made from gelatin, an organic polymer (e.g., polyvinyl alcohol), polyurethanes, polyorthoesters, PLA, PGA, and PLGA copolymers, a saccharide, a calcium salt, sodium chloride, calcium phosphate or mixtures thereof. Porogen particles may be about 100 to about 500 microns.

In one embodiment, all porogen particles of a given morphology can have at least one average axial, transverse, or lateral dimension that is about 100 to about 500 microns. In some embodiments, all porogen particles used can independently have at least one axial, transverse, or lateral dimension that is about 100 to about 500 microns. In some embodiments, all porogen particles used can collectively have at least one average axial, transverse, or lateral dimension that is about 100 to about 500 microns. In some embodiments, at least one dimension of the porogen particles can be about 100 microns or more, or about 120 microns or more, or about 140 microns or more. In some embodiments, at least one dimension of the porogen particles can be about 500 microns or less, about 425 microns or less, about 350 microns or less, about 300 microns or less, or about 250 microns or less. In some embodiments, the porogen particles can have at least one dimension that is about 120 to about 400 microns.

In some embodiments the cohesive mass of fibers could contain single or multiple concentrations of size controlled fibers to affect the consistency of the cohesive mass and affect the handling of the mass after hydration.

In some instances fibers maybe mixed with particles in the cohesive mass to affect the consistency of the cohesive mass and affect the handling of the mass after hydration.

In some instances multiple cohesive masses might be packaged together to improve hydration and/or handling of the cohesive masses prior to and after hydration.

In some instances the cohesive masses may be hydrated with a polar or non-polar solutions and/or salt solutions prior to drying to enhance later rehydration of the mass.

One of more biologically active ingredients may be added to the resulting composition (e.g., lyophilized bone fibers). These active ingredients may or may not be related to the bone repair capabilities of the composition. Suitable active ingredients hemostatic agents, bone morphogenic proteins (BMPs), genes, growth differentiation factors (GDFs), or other non-collagenic proteins such as TGF-β, PDGF, ostropontin, osteonectin, cytokines, and the like.

In one embodiment, the composition may include at least one BMPs, which are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, the particles may include one or more Growth Differentiation Factors ("GDFs") disposed in the compartment or disposed on or in the coherent mass. Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BC030959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BC028237 or AAH28237, as well as mature GDF-10 polypeptides or polynucleotides encoding the same.

GDF-11 polynucleotides or polypeptides corresponding to GenBank Accession Numbers AF100907, NP005802 or 095390, as well as mature GDF-11 polypeptides or polynucleotides encoding the same. GDF-15 polynucleotides or polypeptides corresponding to GenBank Accession Numbers BC008962, BC000529, AAH00529, or NP004855, as well as mature GDF-15 polypeptides or polynucleotides encoding the same.

In some embodiments, the implantable composition contains other bioactive agents which can be delivered with materials of the disclosure. In certain embodiments, the bioactive agent is a drug. These bioactive agents may include, for example, antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergic, anticholinergics, antispasmodics, antiulcer agents, skeletal and smooth muscle relaxants, prostaglandins, general inhibitors of the allergic response, antihistamines, local anesthetics, analgesics, narcotic antagonists, antitus sives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, osteogenic factors, antiarthritics, and diagnostic agents.

A more complete listing of bioactive agents and specific drugs suitable for use in the present disclosure may be found in "The Merck Index: An Encyclopedia of Chemicals, Drugs, and Biologicals," Edited by Susan Budavari, et al.; and the United States Pharmacopoeia/National Formulary XXXVII/XXXII, published by the United States Pharmacopeial Convention, Inc., Rockville, Md., 2013, each of which is incorporated herein by reference.

Bioactive agents may also be provided by incorporation into the implantable composition. Bioactive agents such as those described herein can be incorporated homogeneously or regionally into the implant material by simple admixture or otherwise. Further, they may be incorporated alone or in conjunction with another carrier form or medium such as microspheres or another microparticulate formulation. Suitable techniques for forming microparticles are well known in the art, and can be used to entrain or encapsulate bioactive agents, whereafter the microparticles can be dispersed within the bone graft composite upon or after its preparation.

It will be appreciated that the amount of additive used will vary depending upon the type of additive, the specific activity of the particular additive preparation employed, and the intended use of the composition. The desired amount is readily determinable by the user.

Any of a variety of medically and/or surgically useful substances can be incorporated in, or associated with, the allograft bone material either before, during, or after preparation of the implantable composition. Thus, for example when the non-allograft bone material is used, one or more of such substances may be introduced into the bone fibers, for example, by soaking or immersing these bone fibers in a solution or dispersion of the desired substance(s).

In some embodiments, the cohesive mass of fibers can be lyophilized with one or more growth factors (e.g., BMP, GDF, etc.), drugs so that it can be released from the cohesive mass in a sustained release manner.

Bone Fiber Shapes

The bone fibers can be obtained from bone that is cortical, cancellous or cortico-cancellous of autogenous, allogeneic, xenogeneic, or transgenic origin. This bone can be cartridge milled to obtain the bone fibers of the desired size and diameter. Suitable cartridge mills that can be used to obtain the fibers of desired size and diameter can be obtained from the cartridge mills described in U.S. patent Ser. No. 13/333,279, filed on Dec. 21, 2011 and entitled "OSTEOBIOLOGIC MILLING MACHINE", which was published as U.S. Publication No. 20120160945. This entire disclosure is herein incorporated by reference into the present disclosure, particularly FIG. 2. The milling apparatus described in U.S. Publication No. 20120160945 has a cutter housing and feed chute, a rotary cutter, at least partially housed within the cutter housing and in communication with the feed chute, and a feed ram removably positioned within the feed chute for maintaining a workpiece against the rotary cutter. The feed chute and feed ram may be selectively positionable at one of several angular positions with respect to the rotary cutter. In this manner, the force applied by the feed ram on the workpiece is a function of the weight of the feed ram and the angular position of the feed ram with respect to the rotary cutter. These type of bone milling machines and methods of use result in up to about one-hundred percent (about 100%) workpiece utilization. That is, the bone milling machines described in U.S. Publication No. 20120160945 use the majority of the bone that is placed in the machine and up to one-hundred percent can be used. After milling the bone to the desired fiber size and shape, the bone fiber obtain can subsequently be demineralized.

The present disclosure also provides methods for shaping the coherent mass of fibers as shown, in FIGS. 6-13.

FIG. 5 depicts mineralized fibers having increased surface area. The fibers are milled from bone shafts using any appropriate apparatus, such as a cartridge mill. The fibers are milled to include curled shapes having frayed portions and/or hooked portions to facilitate mechanical interlocking of the fibers. For example, as shown in FIG. 5, milling the bone material creates fibers 74 and bone particles 76 separate from the fiber. The shape of the allograft may be tailored to fit the site at which it is to be situated. For example, it may be in the shape of a morsel, a plug, a pin, a peg, a cylinder, a block, a wedge, ring, a sheet, etc.

In one embodiment, the method comprises placing allograft bone fibers into a mold prior to demineralization and/or lyophilization. The fibers are then demineralized, sterilized and/or lyophilized to create a shaped coherent mass of fibers, as shown in FIGS. 6-13. The fibers can be placed into a mold and then subjected to demineralization and/or lyophilization to make the desired shape or the fibers can be demineralization and/or lyophilization and then shaped by stamping or punching the desired shape. The demineralization and lyophilization steps alter the shape of the fibers to facilitate entanglement and mechanical interlocking, as discussed herein. Thus, in some embodiments, the fibers are shaped into a coherent mass through being subjected to demineralization and/or lyophilization while in a molded cavity (not shown). The fibers form such a coherent mass without the use of a binding agent or carrier.

In some embodiments, the fibers are placed into molds and shaped to form a coherent mass in a range of predetermined shapes and sizes according to the needs of a medical procedure. In some embodiments, the allograft may be made by injection molding, compression molding, die pressing, slip casting, laser cutting, water-jet machining, sand casting, shell mold casting, lost tissue scaffold casting, plaster-mold casting, vacuum casting, permanent-mold casting, slush casting, pressure casting, die casting, centrifugal casting, squeeze casting, rolling, forging, swaging, extrusion, shearing, spinning, or combinations thereof.

Figure 8:
FIG. 8 depicts the bone material in a disc shape unit. Similarly to the coherent mass in FIG. 7, coherent mass 70 is formed after demineralization and then placing the fibers in a mold and then lyophilization. Alternatively, the coherent mass can be punched or stamped into the desired shape and then lyophilized or lyophilized after demineralization and then punched or stamped into the desired shape. The coherent mass 70 is in a disc shape and includes a reservoir 72 to facilitate hydration.

The fibers may be molded into a disc shaped cohesive mass 70 having a reservoir 72 to facilitate hydration, as shown in FIG. 8. Cohesive mass 70 may include a uniform thickness or a variable thickness across its surface to facilitate packaging and/or hydration. Reservoir 72 comprises a depressed area on a surface of cohesive mass 70 to hold liquid during hydration. As shown in FIG. 8, reservoir 72 comprises a circular shape. However, in other embodiments, the reservoir may include variable cross sectional shapes, such as polygonal, oval or irregular.

Figure 9:
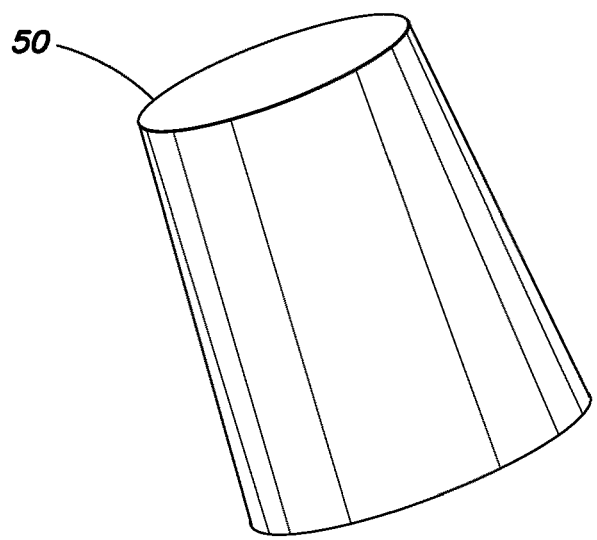
FIG. 9 depicts the bone material in a plug shape.

The fibers may be molded into a conical or plug shape to form a coherent mass 50, as shown in FIG. 9. Coherent mass 50 includes a first end having a first diameter and a second end having a second diameter. In some embodiments, the first diameter is wider than the second diameter.

Figure 10:
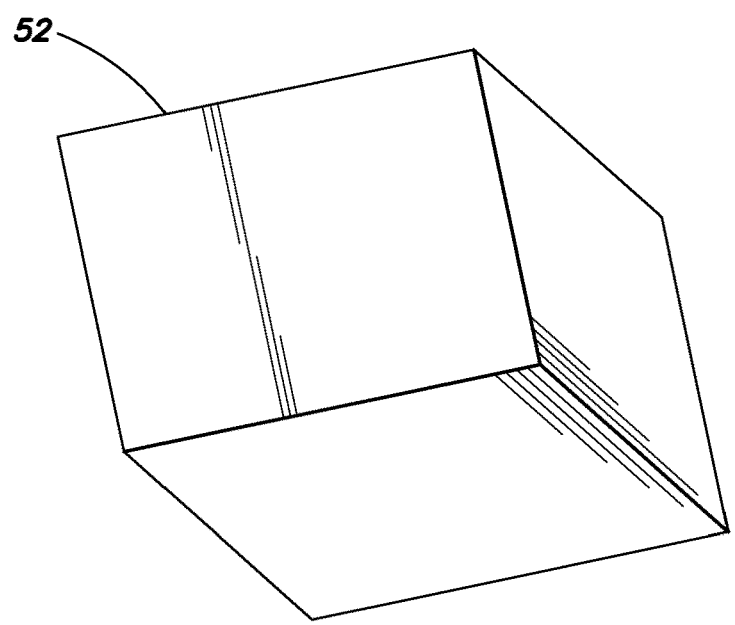
FIG. 10 depicts the bone material in a cube shape.

The fibers may be molded into a cube shape to form a coherent mass 52, as shown in FIG. 10. In other embodiments, the coherent mass may include other prismatic configurations, similar to coherent mass 52. For example, the coherent mass may be rectangular, pyramidal, triangular, pentagonal, or other polygonal or irregular prismatic shapes.

Figure 11:
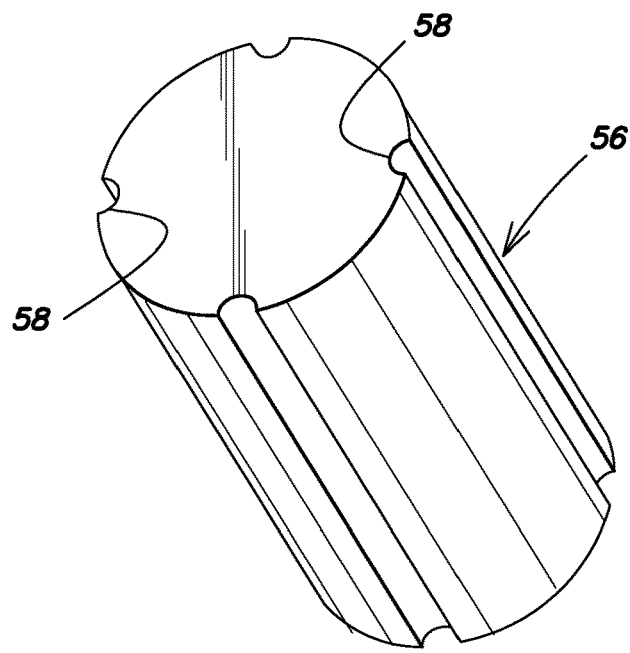
FIG. 11 depicts the bone material in a cylindrical shape having hydration channels to facilitate hydration.

The fibers may be molded into a cylindrical shape to form a coherent mass 56, as shown in FIG. 11. Coherent mass 56 includes a first end having a first diameter and a second end having a second diameter. In some embodiments, the first diameter is the same as the second diameter.

The fibers may be molded into a cylindrical shape to form a coherent mass 56 that has external hydration channels 58, as shown in FIG. 11. Coherent mass 56 includes a first end having a first diameter and a second end having a second diameter. In some embodiments, the first diameter is wider than or the same size as the second diameter. Hydration channels 58 are present on an outer surface of coherent mass 56 and are configured to facilitate entrance of a hydrating liquid into coherent mass 56, as discussed herein. External hydration channels 58 include a rounded inner surface formed from drilling or pressing. However, in other embodiments, channels 58 may be slotted and include straight inner surfaces. The fibers are porous and the liquid can pass through the coherent mass, however, hydration channels 58 enhance the passage of fluid.

Figure 12:
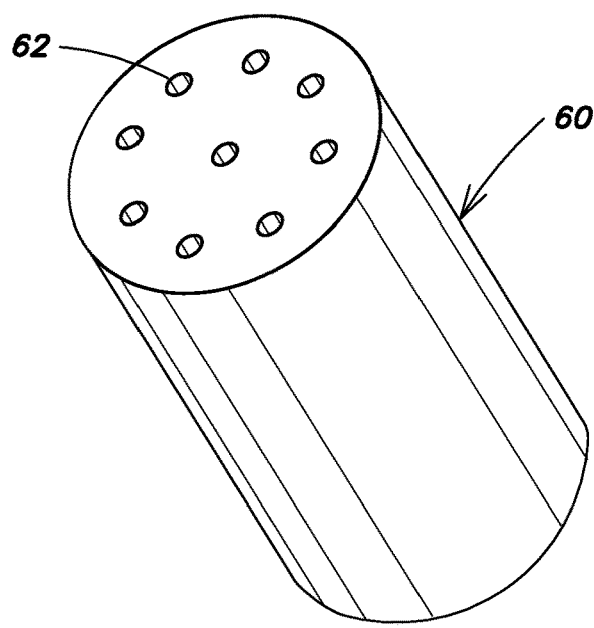
FIG. 12 depicts the bone material in a cylindrical shape. The bone material includes external hydration channels 58 to facilitate hydration.

The fibers may be molded into a cylindrical shape to form a coherent mass 60 that has internal hydration channels 62, as shown in FIG. 12. Coherent mass 60 includes a first end having a first diameter and a second end having a second diameter. In some embodiments, the first diameter is wider than or the same size as the second diameter. Hydration channels 62 extend through at least a portion of coherent mass 60 and are configured to facilitate entrance of a hydrating liquid into coherent mass 60, as discussed herein. Internal hydration channels 62 include a rounded inner surface formed from drilling or pressing. The fibers are porous and the liquid can pass through the coherent mass, however, hydration channels 62 enhance the passage of fluid into the implant.

Figure 13:
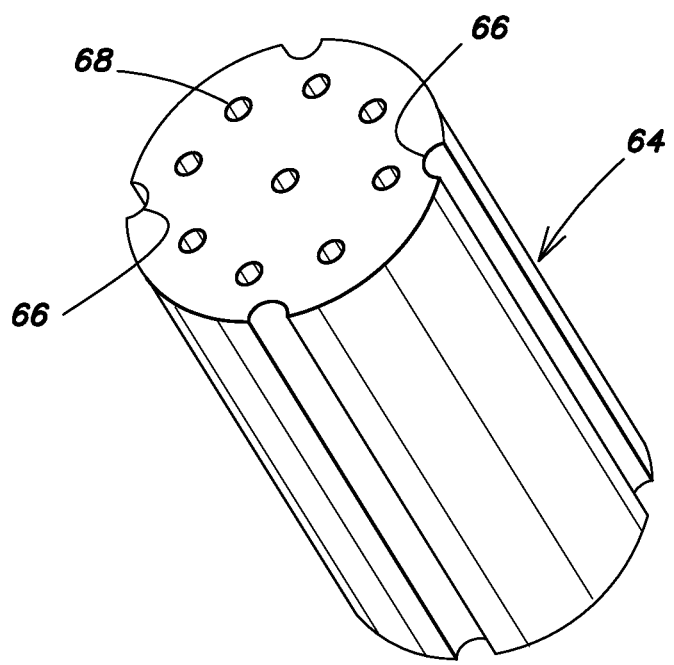
FIG. 13 depicts the bone material in a cylindrical shape. The bone material includes a combination of external hydration channels 66 and internal hydration channels 68 to facilitate hydration of coherent mass 64.

The fibers may be molded into a conical or plug shape to form a coherent mass 64 that has external hydration channels 66 and internal hydration channels 68, as shown in FIG. 13. Coherent mass 64 includes a first end having a first diameter and a second end having a second diameter. In some embodiments, the first diameter is wider than or the same as the second diameter. External hydration channels 66 are present on an outer surface of coherent mass 64, and internal hydration channels 68 extend through at least a portion of coherent mass 64. Hydration channels 66, 68 are configured to facilitate entrance of a hydrating liquid into coherent mass 64, as discussed herein. Hydration channels 66, 68 include a rounded inner surface formed from drilling or pressing.

Demineralization

After the bone is obtained from the donor and milled into a fiber, it is processed, e.g., cleaned, disinfected, defatted, etc., using methods well known in the art. The entire bone can then be demineralized or, if desired, the bone can just be sectioned before demineralization. The entire bone or one or more of its sections is then subjected to demineralization in order to reduce the inorganic content to a low level, e.g., to contain less than about 10% by weight, preferably less than about 5% by weight and more preferably less than about 1% by weight, residual calcium.

DBM may be prepared in any suitable manner. In one embodiment, the DBM is prepared through the acid extraction of minerals from bone. It includes the collagen matrix of the bone together with acid insoluble proteins including bone morphogenic proteins (BMPs) and other growth factors. It can be formulated for use as granules, gels, sponge material, putty, or paste and can be freeze-dried for storage. Sterilization procedures used to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues. As noted, in embodiments of bone particles taken from cortical long bones, the osteoinductive potential of the bone particles when demineralized may vary based on the source of the bone particles, whether from the periosteal layer, the middle layer, or the endosteal layer.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In one demineralization procedure, the bone is subjected to an acid demineralization step followed by a defatting/disinfecting step, where the coherent mass of bone fiber can be formed. The bone is immersed in acid to effect demineralization. Acids that can be employed in this step include inorganic acids such as hydrochloric acid and as well as organic acids such as formic acid, acetic acid, peracetic acid, citric acid, propionic acid, etc. The depth of demineralization into the bone surface can be controlled by adjusting the treatment time, temperature of the demineralizing solution, concentration of the demineralizing solution, and agitation intensity during treatment. Thus, in various embodiments, the DBM may be fully demineralized, partially demineralized, or surface demineralized.

The demineralized bone is rinsed with sterile water and/or buffered solution(s) to remove residual amounts of acid and thereby raise the pH. A suitable defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily, at least about 10 to 40 percent by weight of water (i.e., about 60 to 90 weight percent of defatting agent such as alcohol) is present in the defatting disinfecting solution to produce optimal lipid removal and disinfection within a given period of time. A suitable concentration range of the defatting solution is from about 60 to about 85 weight percent alcohol, or about 70 weight percent alcohol.

In some embodiments, the demineralized bone may be further treated to effect properties of the bone. For example, the DBM may be treated to disrupt the collagen structure of the DBM. Such treatment may comprise collagenase treatment, heat treatment, mechanical treatment, or other. Reference is made to U.S. Provisional Patent Applications 60/944,408, 60/944,417, and 60/957,614, herein incorporated by reference, for further treatment options.

Lyophilization

The bone fibers are lyophilized either in a mold for a desired shape or out of a mold, where in can be shaped (e.g., stamped, punched, cut, etc.). For example, the bottle containing bone and conserving agent is initially frozen to −76° C. with the bone and conserving agent later being subjected to a vacuum of less than 100 militorr while the temperature is maintained at or below −35° C. The end point of the lyophilization procedure is the determination of residual moisture of approximately 5%. Once the bone has been lyophilized, it is stored in sealed, vacuum-contained, bottles prior to its reconstitution and use.

In some embodiments, the demineralization and lyophilization steps alter the shape of the fibers to facilitate entanglement and mechanical interlocking. Thus, in some embodiments, the fibers are shaped into a coherent mass through being subjected to demineralization and/or lyophilization while in a molded cavity (not shown). The fibers form such a coherent mass without the use of a binding agent or carrier. For example, as shown in FIGS. 6, the individual fibers 82 form a coherent mass 78 after the demineralization and lyophilization steps. During lyophilization of fibers 82, frayed/hooked portions 80 become increasingly tangled with each other to increase mechanical interlocking of the fibers.

To facilitate on-site preparation and/or usage of the composition herein, the demineralized fibrous bone elements and non-fibrous bone elements, preferably in lyophilized or frozen form, and fluid carrier (the latter containing one or more optional ingredients such as those identified above) can be stored in separate packages or containers under sterile conditions and brought together in intimate admixture at the moment of use for immediate application to an osseous defect site employing any suitable means such as spatula, forceps, syringe, tamping device, and the like. Alternatively, the implant composition can be prepared well in advance and stored under sterile conditions until required for use. When the implant composition is prepared well in advance it is preferably lyophilized prior to packaging for storage. In some embodiments, the composition described herein can be combined with autograft bone marrow aspirate, autograft bone, preparations of selected autograft cells, autograft cells containing genes encoding bone promoting action prior to being placed in a defect site. In various embodiments, the implant composition is packaged already mixed and ready for use in a suitable container, such as for example, syringe, resealable non-toxic bottle, a bag mesh or pouch or is provided as a kit which can be prepared at a surgeon's direction when needed.

Hydration

Figure 7:
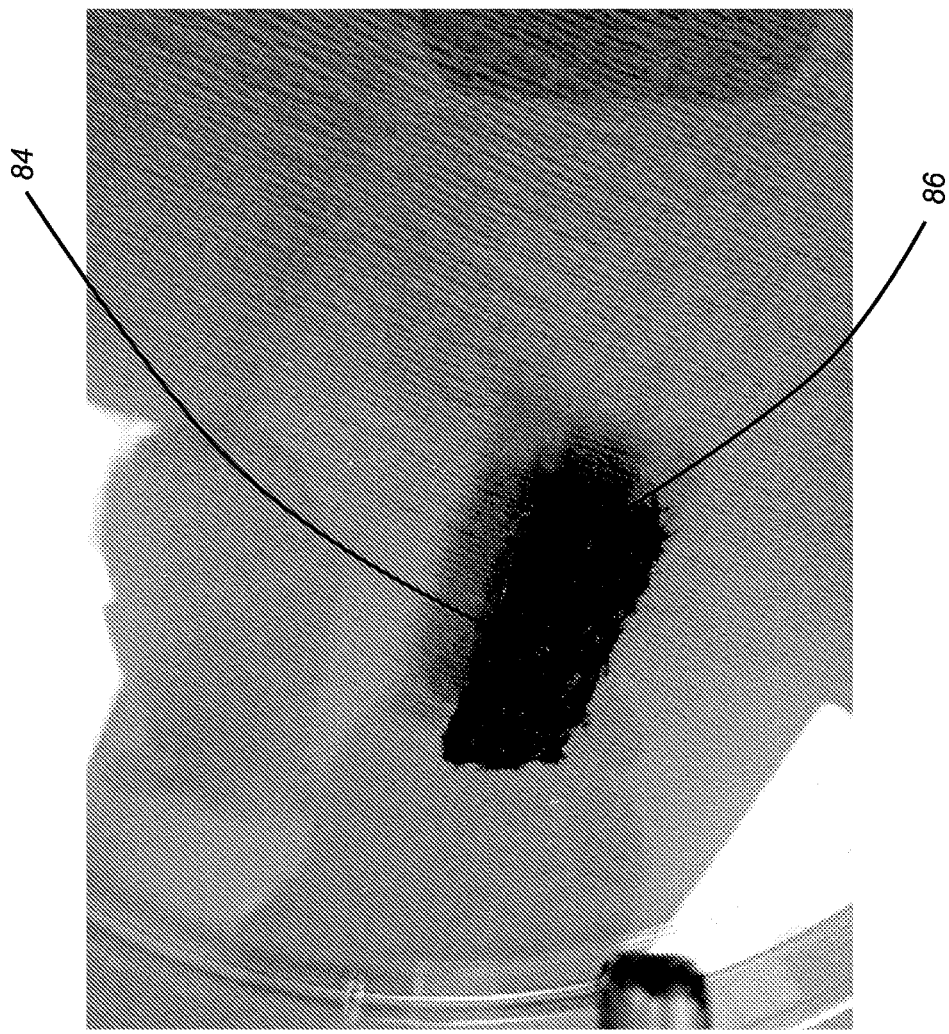
FIG. 7 depicts the bone material in a cylindrical shape. After the bone fibers are milled, the fibers are demineralized and subsequently placed into a mold or punch and lyophilized to form a coherent mass 84 in a cylindrical shape having a hydration channel 86. The coherent mass 84 may be hydrated by a liquid such as blood, water or saline.

As shown, for example, in FIG. 7, following demineralization and/or lyophilization, the coherent mass is hydrated to turn the molded coherent mass into a moldable and malleable putty or paste. In some embodiments, the coherent mass is hydrated with water, saline and/or blood. Once hydrated, the coherent mass is placed into a surgical site at a location determined by a medical practitioner. The fibers in the coherent mass maintain their coherency and mechanical interactions such that the putty or paste requires no binding agent or carrier when placed in situ. In some embodiments, the fibers of the coherent mass are hydrophobic and internal or external hydration channels facilitate hydration of the coherent mass.

In some embodiments, the coherent mass may be hydrated with PBS or other physiologically acceptable fluid, and provided for use in a hydrated form. The coherent mass may be placed at a surgical site directly and subsequently hydrated, or it can be hydrated to form a wet paste and subsequently implanted at a surgical site.

A physiologically acceptable liquid, in some embodiments containing water, may be added to the bone repair composition prior to placement into the site or defect. Such physiologically acceptable liquids include those discussed above, including physiological saline or a blood product. Blood products include whole blood and blood fractions such as platelet rich plasma and platelet poor plasma.

In some embodiments, the bone repair composition is hydrated with a physiologically acceptable liquid and biocompatible carrier. Non-limiting examples of physiologically acceptable liquids include saline, phosphate buffered saline (PBS), hyaluronic acid, cellulose ethers (such as carboxymethyl cellulose), collagen, gelatin, autoclaved bone powder, osteoconductive carriers, whole blood, blood fractions, bone marrow aspirate, concentrated bone marrow aspirate, and mixtures thereof. Non-limiting examples of blood fractions include serum, plasma, platelet-rich plasma, concentrated platelet-rich plasma, platelet-poor plasma, and concentrated platelet poor plasma. After hydrating, the bone repair composition becomes a putty or a paste that can be molded into a predetermined shape or administered to a bone defect and manipulated to conform to the bone defect in such a manner that will promote healing. For example, the composition may be hydrated with about 2 ml of saline blood per 2.5 g of combined DBM and periosteal powder.

In some embodiments, the bone material can be hydrated by from about 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, 60 to about 99.9% w/v, w/w and/or v/v hydrated with the fluid to the desired consistency.

Mixing Device

In various embodiments, a device 10 for mixing a bone material with a liquid is provided, as shown in FIGS. 1-4. The device comprises a first syringe 12 comprising a first chamber 14 having a proximal end 16 and a distal end 18. The first chamber comprises a syringe barrel. A bone material 22 is disposed within the chamber. The bone material comprises a coherent mass of milled and lyophilized demineralized bone fibers. The first syringe comprises a plunger 20 having at least a portion slidably disposed within the proximal end of the chamber and configured to dispense the bone material when mixed with a liquid from the distal end of the chamber, when the plunger is in an extended position.

Device 10 includes a second syringe 24 comprising a second chamber 26 having a proximal end 28 and a distal end 30. The second chamber comprises a syringe barrel. A liquid 34 is disposed within the second chamber. The liquid is configured to hydrate the coherent mass of milled and lyophilized demineralized bone fibers. In some embodiments, the liquid comprises blood, water, saline or a combination thereof. The second syringe comprises a second plunger 32 having at least a portion slidably disposed within the proximal end of the second chamber.

Device 10 includes a connector 36 fluidly coupling the distal end of the first chamber to the distal end of the second chamber via a dispensing channel 19 and a hydrating channel 21 of the connector 36. The dispensing channel is coupled to the distal end of the first chamber and the hydrating channel is coupled to the distal end of the second chamber.

Figure 2:
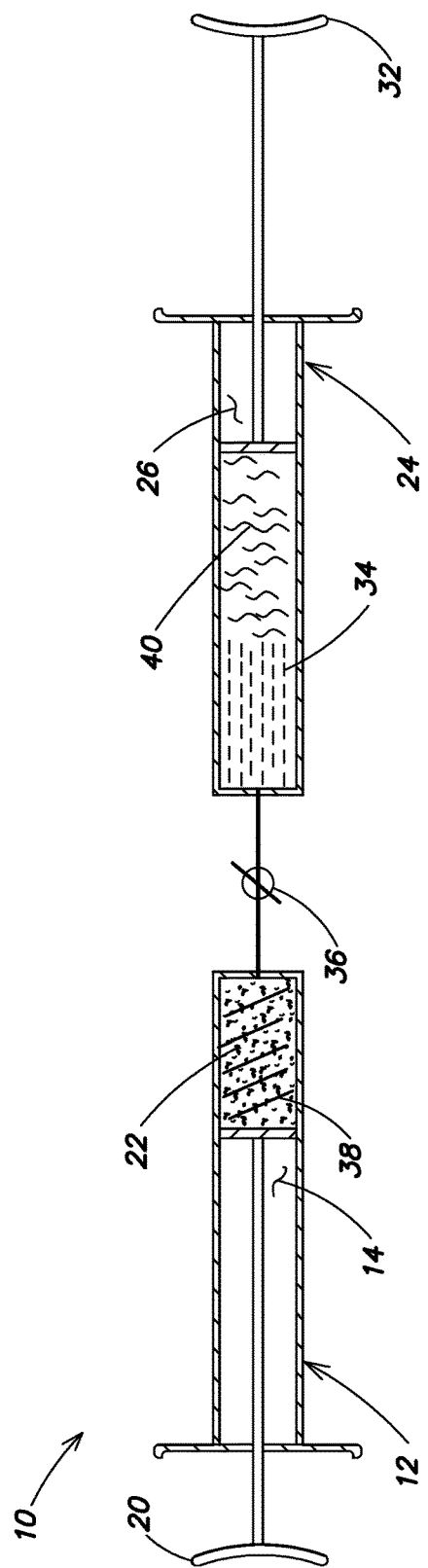
FIG. 2 depicts the mixing device of FIG. 1. Movement of the second plunger to an retracted position causes a gas (e.g., air) to move from the bottom of the chamber to the top of the chamber near the plunger in the second chamber containing the liquid, which causes a vacuum or negative pressure to be generated in the first chamber that contains the coherent mass of milled and lyophilized demineralized bone fibers.
Figure 3:
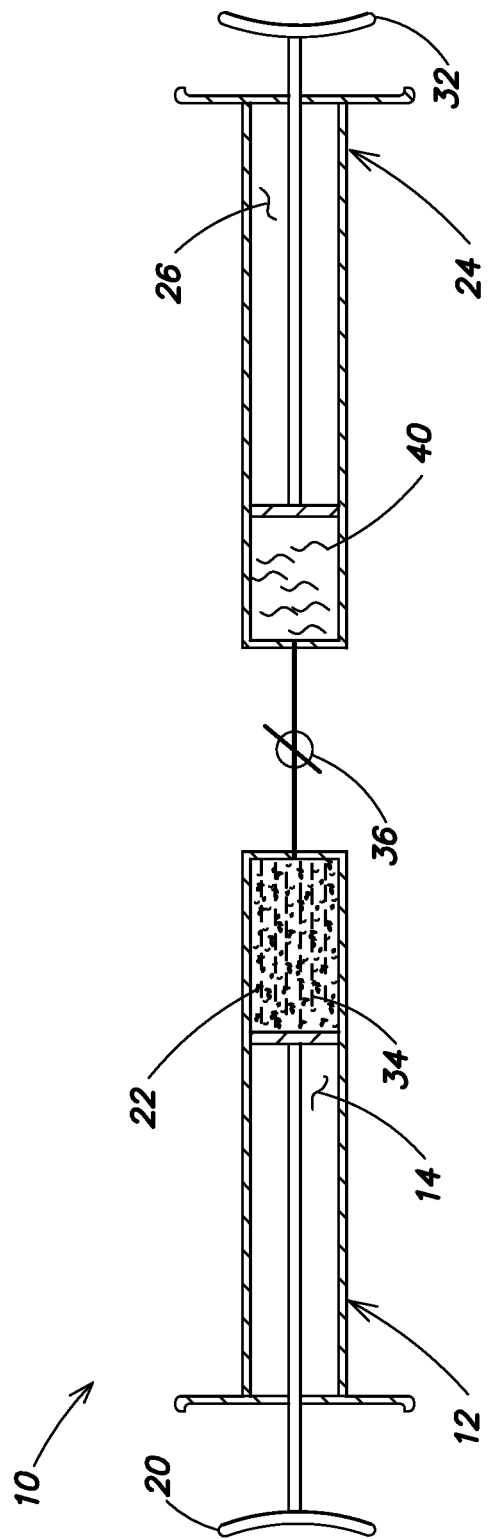
FIG. 3 depicts the mixing device of FIG. 1. The movement of the second plunger to an extended position causes a gas to move into the second chamber and mix with the liquid and cause fluid to enter the connector and into the first chamber by the vacuum or negative pressure generated in the first chamber. This will hydrate the bone material in the first chamber and form a moldable coherent mass of milled and lyophilized demineralized bone fibers.
Figure 4:
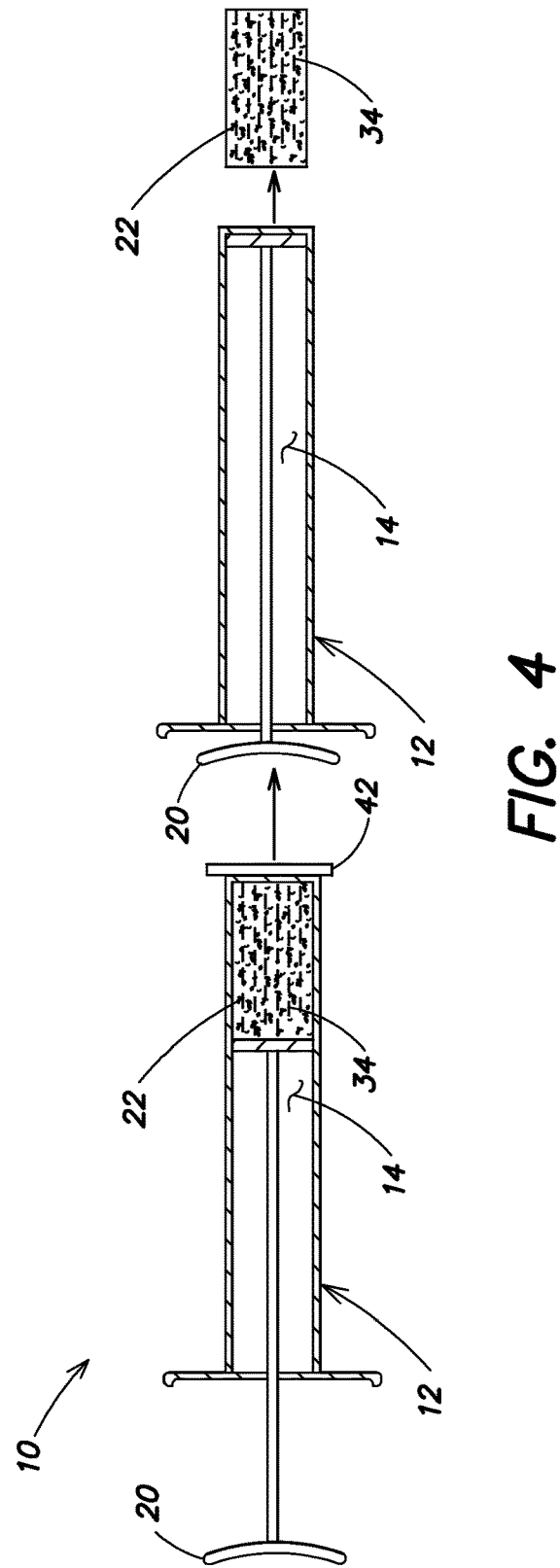
FIG. 4 depicts another embodiment of the mixing device. The hydrated bone material is encased in the first chamber of the first syringe. A cap attached to an end of the chamber is removed and the hydrated bone material is ejected from the first chamber. The hydrated bone material becomes a moldable putty that can be injected into a surgical site.

Movement of the second plunger to an extended position, as shown in FIG. 2 causes negative pressure 38 (e.g., a vacuum) to be created in the first chamber and the liquid disposed in the second syringe to flow.

The movement of the second plunger to a retracted position, as shown in FIG. 2 forces a gas 40 to move into the second chamber and mix with the liquid. The air and liquid is displaced and pressure is generated in the second chamber causing the second plunger to move in the extended position to cause the fluid to enter the connector's hydrating channel and dispensing channel, and into the first chamber to replace the space from the vacuum. The liquid is mixed with the lyophilized demineralized bone fibers using the negative pressure created in the first chamber by the plunger. The hydration fluid can be 1 mL, 2 mL, 3 mL, 4 mL, 5 mL, 6 mL, 7 mL, 8 mL, 9 mL, 10 mL of fluid or greater. This will hydrate the coherent mass of milled and lyophilized demineralized bone fibers in the first chamber because it is porous. In some embodiments, the coherent mass of milled and lyophilized demineralized bone fibers is hydrated in about 60 seconds. In some embodiments, the coherent mass of milled and lyophilized demineralized bone fibers is hydrated in more than 60 seconds. In some embodiments, the coherent mass of milled and lyophilized demineralized bone fibers is hydrated in about 1, 2, 3, 4, 5, 6, 7, 8, 9 or 10 minutes.

The first chamber is detachable from the connector to dispense the hydrated coherent mass of milled and lyophilized demineralized bone fibers that is moldable to a surgical site. When the first chamber is detached, a cap 42 connected to the distal end of the chamber is removed and the hydrated coherent mass of milled and lyophilized demineralized bone fibers is ejected from the first chamber.

In some embodiments, the coherent mass of milled and lyophilized demineralized bone fibers does not contain a binder. In some embodiments, the coherent mass of milled and lyophilized demineralized bone fibers comprises cartridge milled fibers having a curled portion. In some embodiments, the coherent mass of milled and lyophilized demineralized bone fibers comprises autograft or allograft bone. In some embodiments, the bone fibers have a diameter from about 100 μm to about 2 mm.

In various embodiments, the bone fibers have a length from about 0.5 mm to about 50 mm. In some embodiments, the bone fibers have an average length from about 0.5 cm to about 10 cm.

In some embodiments, the fibers have an aspect ratio of from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1.

In various embodiments, a method of hydrating a bone material with a liquid is provided. The method comprises mixing the liquid with the bone material comprising a coherent mass of milled and lyophilized demineralized bone fibers in a device. The device comprises a first chamber having a proximal end and a distal end, and the bone material is disposed within the first chamber. A first plunger is provided having at least a portion slidably disposed within the proximal end of the first chamber. The device comprises a second chamber having a proximal end and a distal end. The liquid is disposed within the second chamber. The liquid is configured to hydrate the coherent mass of milled and lyophilized demineralized bone fibers. A second plunger is provided having at least a portion slidably disposed within the proximal end of the second chamber. The device comprises a connector fluidly coupling the distal end of the first chamber to the distal end of the second chamber, wherein movement of the second plunger to an extended position causes liquid to flow to hydrate the coherent mass of milled and lyophilized demineralized bone fibers in the first chamber.

The first chamber is detached from the connector to dispense the hydrated coherent mass of milled and lyophilized demineralized bone fibers that is moldable.

Referring to FIGS. 14-17, FIG. 14 depicts another embodiment of a mixing device for mixing a bone material 122 with a liquid 134. The mixing device comprises a first syringe 112 and a second syringe 124. The first syringe comprises a bone material comprising a coherent mass of milled and lyophilized demineralized bone fibers. The second syringe 124 comprises a liquid 134, such as blood, saline, sterile water, dextrose, or combination thereof or other physiological fluid that can be used to hydrate the bone material to make it the desired consistency (e.g., moldable putty, paste, gel, etc.). The syringes are connected via a connector 136. The first and second syringes can engage the connecter via threading 137, suitable threadings can be in a leur lock fitting, alternatively, there can be a friction or snap-fit fitting so that the syringes can engage the connector and provide a seal that prevents leakage of fluid. In some embodiments, the threading 137 extends radially at discrete positions in the interior of the connector and is configured to engage reciprocal threading of the first and/or second syringe to provide an air tight seal.

Figure 14:
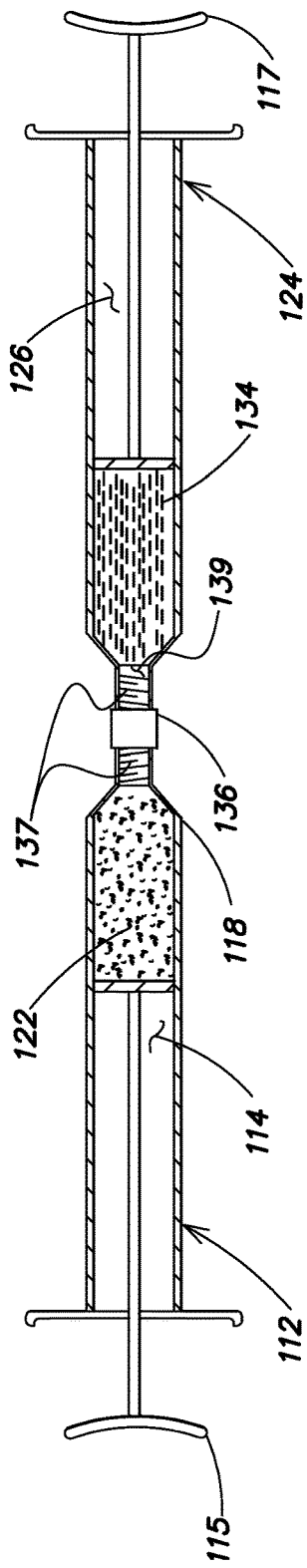
FIG. 14 depicts another embodiment of a mixing device for mixing a bone material with a liquid. The mixing device comprises a first syringe and a second syringe. The first syringe comprises a bone material comprising a coherent mass of milled and lyophilized demineralized bone fibers. The second syringe comprises a liquid. The syringes are connected via a connector.

In FIG. 14, to hydrate the bone material, sliding the second plunger 117 longitudinally in the second chamber 126 of the second syringe 124 causes the liquid 134 to enter channel 139 of the connector 136, which causes liquid and any gas in the second chamber 126 to enter first chamber 114 of first syringe 112 through the distal end 118 of first syringe to hydrate the bone material. As the second plunger tip 111 is moved in an extended position and longitudinal closer in distance to the connector, the liquid and air is expelled from the second syringe into the channel 139 of the connector and into the first chamber 114 of the first syringe 112 to hydrate the bone material. Due to the transfer of pressure and volume from the liquid and air in the second syringe to the first syringe through the connector, the first plunger tip 110 and the first plunger 115 is slidably moved longitudinally in a retracted position, where the first plunger tip 110 is moved a farther distance from the connector as the bone material is hydrated. It will be understood that the first and second syringes, plunger, plunger tip and connector can be made of metal or disposable material, such as for example plastic.

In some embodiments, the device can be monolithic and a single piece. In some embodiments, the first plunger 115 and second plunger 117 can have handles to allow easier mixing between the second chamber 126 and the first chamber 114. The plungers can be slid longitudinally in their respective chambers one or more times to allow mixing and hydration of the bone material between first and second chambers so as to provide the desired hydration of the bone material.

Figure 15:
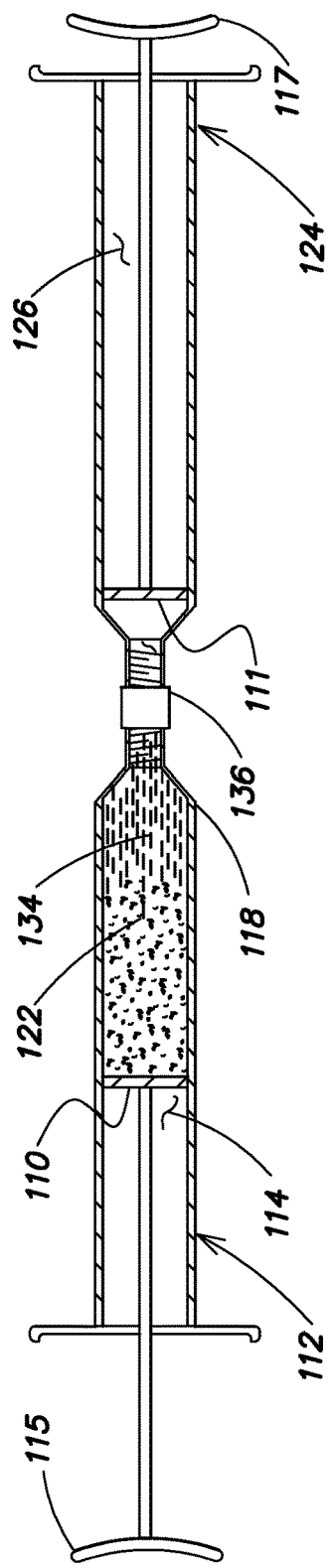
FIG. 15 depicts the mixing device of FIG. 14. Movement of the second plunger tip to an extended position, which is a closer distance longitudinally to the connector, causes a gas (e.g., air) and liquid to move from the bottom of the chamber to the top of the chamber and through the connector to the first syringe and first chamber to hydrate the coherent mass of milled and lyophilized demineralized bone fibers. For the additional volume, the plunger in the first chamber will move in a retracted position, farther in distance longitudinally from the connector, so as to aid in the hydration of the lyophilized demineralized bone fibers.

FIG. 15 depicts the mixing device of FIG. 14. Slidable movement of the second plunger 117 longitudinally causes second plunger tip 111 to move in an extended position, which is a closer distance longitudinally to the connector 136, which causes a gas (e.g., air) and liquid to move from the bottom of the second chamber 126 of the second syringe 124 to the top of the chamber and through the connector 136 to the first syringe 112 and first chamber 114 to hydrate the coherent mass of milled and lyophilized demineralized bone fibers with liquid 134. For the additional volume, the plunger 115 and first plunger tip 110 in the first chamber 114 will move in a retracted position, farther in distance longitudinally from the connector 136 and distal end 118, so as to aid in the hydration of the bone material 122 (e.g., lyophilized demineralized bone fibers). Shown in FIG. 15 is the second chamber 126 of the second syringe 124 empty and substantially free of air and liquid. The second plunger is in an extended position. The liquid (e.g., blood, saline, dextrose, or other physiological fluid, etc.) is in the first syringe and the bone material is being hydrated.

Figure 16:
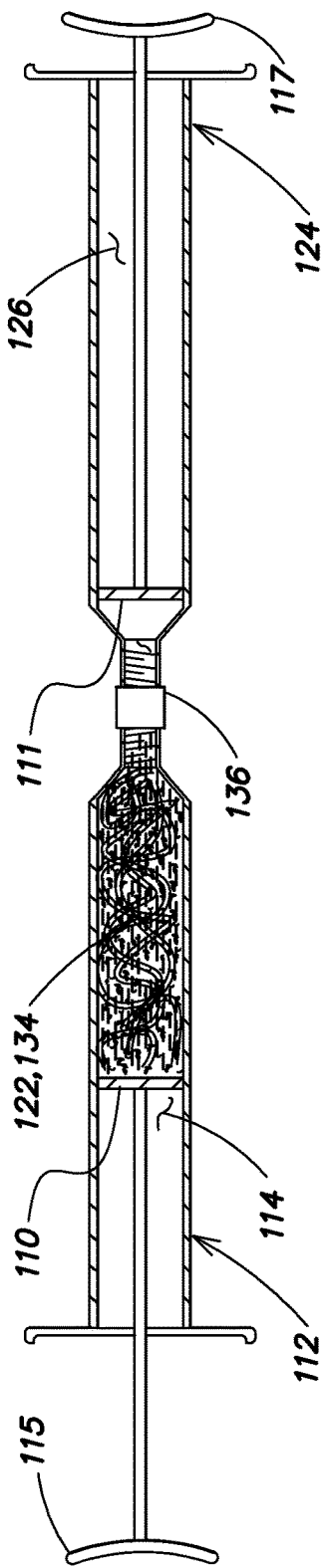
FIG. 16 depicts the mixing device of FIG. 14. The movement of the second plunger to an extended position, which is a closer distance longitudinally to the connector, causes a gas to move into the second chamber and mix with the liquid and cause fluid to enter the connector and into the first chamber. This will hydrate the bone material in the first chamber and form a moldable coherent mass of milled and lyophilized demineralized bone fibers. In some embodiments, after the second plunger is moved, the first plunger can be moved in an extended position, which is a closer distance longitudinally to the connector, causing the mixed bone material, gas and liquid to move out of the first chamber through the connector and into the second chamber and further mix the bone material, liquid and gas to further hydrate the bone material. These steps can be repeated one or more times transferring the bone material, fluid and any air between first and second syringes and the connector until the desired hydration of the bone material is achieved.

FIG. 16 depicts the mixing device of FIG. 14. The movement of the second plunger 117 to an extended position, which is a closer distance longitudinally to the connector 136, causes a gas to move into the second chamber 126 and mix with the liquid and cause fluid to enter the connector 136 and into the first chamber 114 of the first syringe 112. This will hydrate the bone material 134 in the first chamber and form a moldable coherent mass of milled and lyophilized demineralized bone fibers hydrated with liquid 122. In some embodiments, after the second plunger 117 is moved longitudinally in an extended position closer to the connector 136, the first plunger 115 can be moved in a retracted position, which is a farther distance longitudinally from the connector. This can be passive movement based on the pressure exchange or active movement by the user applying appropriate force to move the first and/or second plunger. In some embodiments, after the second plunger is moved, the first plunger can be moved in an extended position, which is a closer distance longitudinally to the connector, causing the mixed bone material, gas and liquid to move out of the first chamber through the connector and into the second chamber and further mix the bone material, liquid and gas to further hydrate the bone material. These steps can be repeated one or more times transferring the bone material, fluid and any air between first and second syringes and the connector until the desired hydration of the bone material is achieved. It will be understood that the first plunger 115 and/or the second plunger 117 can be removed from their respective syringes and the material can be added to the syringe and the plunger slidably inserted into the respective chamber. Alternatively, each syringe can be filled with the desired material (e.g., bone material in the first syringe or fluid in the second syringe) by sliding the plunger longitudinally away from the syringe's distal end to draw up the material into the syringe chamber. The syringes can then be attached to the connector by the fitting (e.g., threading, friction fitting, etc.) for mixing.

FIG. 17 depicts the first syringe 112 of the mixing device of FIG. 14. The first syringe is removed from the connector. The hydrated bone material (bone material 122 and liquid 134) is encased in the first chamber 114 of the first syringe, which is capped by cap 140. Cap 140 attached to a distal end 113 of the first syringe 112 is removed and the hydrated bone material is ejected or extruded from the first chamber of the first syringe. The hydrated bone material (bone material 122 and liquid 134) becomes a moldable putty or paste that can be injected or implanted into a surgical site. Threading at the distal tip 113 is reciprocal threading and configured to engage the corresponding threading 137 of the connector 136 of FIG. 14.

In some embodiments, the second syringe with fluid can be docked to the first syringe that contains the bone material (e.g., bone graft material to be hydrated). Fluid from the second syringe is introduced into the first syringe that contains the bone graft material and the bone material is hydrated. The second syringe having no more fluid is removed. The first syringe having the bone material and fluid in it is capped. The plunger of the first syringe containing the fluid and the bone material is moved multiple times to pressurize the device and force fluid into graft for the desired hydration. The cap is then removed and the hydrated bone material is removed.

Referring to FIGS. 18A-18C, FIG. 18A illustrates a perspective view of an embodiment of a connector 150 that can engage the first and second syringe. The connector has openings 152 and 154 that each have a diameter that is the same or less than the diameter of the first and second syringe. The connector provides a fluid seal and acts as a conduit between the two syringes. This is ideal for mixing. The connector can be plastic or metal or a combination thereof. FIG. 18B illustrates a cross-sectional view of the connector 150 having threading 156 and 158 that can engage the first and second syringe. The user takes first syringe with corresponding threading and engages threading 156 and takes second syringe with corresponding threading and engages threading 158 by turning the syringe or connector clockwise or counter clockwise until the device is assembled to provide an air-tight seal. Channel 157 acts as a conduit for mixing the material between syringes. FIG. 18C illustrates a side perspective view of the connector having channels that can engage the first syringe. The channel 157 can have an extension member 160 shown as a cross to create turbulent flow between first and second syringes and connector 150 to aid in mixing the components. Alternatively or in addition to the extension member, there can be a valve disposed in the channel to change flow rates between first and second syringes and the connector. In some embodiments, the valve can be a flap valve, duck-bill valve or the like and can partially or completely occlude the channel of the connector. The valve is responsive to pressure in the connector and can move in the direction of flow and pressure. Projection 161 can be radially arrayed at discrete regions of the outer surface of the connector 150 to allow easier engagement of the connector by hand or machine.

Referring to FIGS. 19A-19C, FIG. 19A illustrates a perspective view of an embodiment of the connector 162 that can engage the first and second syringe. The connector has openings 166 and 164 that each have a diameter that is the same or less than the diameter of the first and second syringe. The connector provides a fluid seal and acts as a conduit between the two syringes. This is ideal for mixing. The connector can be plastic or metal or a combination thereof. FIG. 19B illustrates a cross-sectional view of the connector 162 having threading 170 and 168 that can engage the first and second syringe. The user takes first syringe with corresponding threading and engages threading 170 and takes second syringe with corresponding threading and engages threading 168 by turning the syringe or connector clockwise or counter clockwise until the device is assembled to provide an air-tight seal. Channel 169 acts as a conduit for mixing the material between syringes.

In some embodiments, the connector 162 comprises a channel 169 that is a smaller diameter than openings 166 and 164. This smaller diameter provides an air-tight seal with the syringes and also increases pressure when force from the plunger is applied to the syringe due to the liquid and/or bone material entering into a smaller area of the connector, such design aids in mixing the components. The threading 170 and 168 are radially arrayed about the interior of the connector and are configured to engage reciprocating threading of the syringe. Alternatively, there can be a friction fitting, such as for example, a snap-fit syringe tip, where the syringe has no threading but can engage the connector and slide therein to provide the air tight seal. It will be understood that optimum flow of material is reached when the channel, opening and syringe chambers are aligned.

FIG. 19C illustrates a side perspective view of the connector having a channel that can engage the first syringe. The channel 169 can have a smaller diameter relative to the diameter of the syringe to create more pressure and a turbulent flow between first and second syringes and connector 162 to aid in mixing the components. Alternatively or in addition to the extension member, there can be a valve disposed in the channel to change flow rates between first and second syringes and the connector. Projection 166 can be radially arrayed at discrete regions of the outer surface of the connector 162 to allow easier engagement of the connector by hand or machine.

Figure 20B:
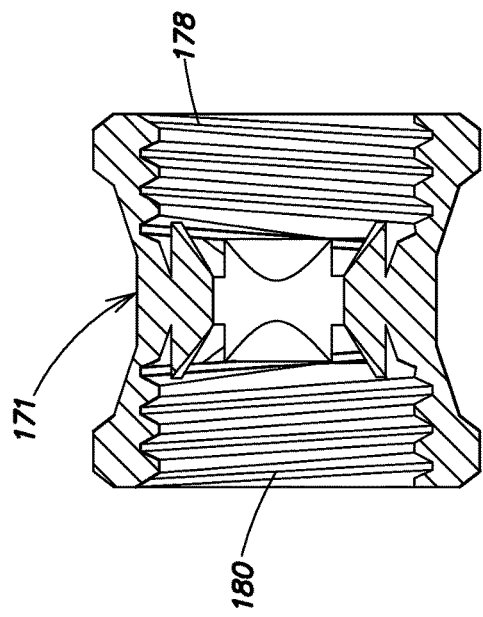
FIG. 20B illustrates a cross-sectional view of the connector having threading that can engage the first and second syringe.
Figure 20C:
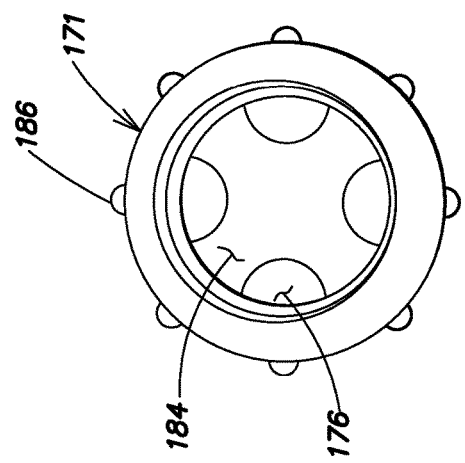
FIG. 20C illustrates a side perspective view of the connector having a channel that can engage the first or second syringe.
Figure 20A:
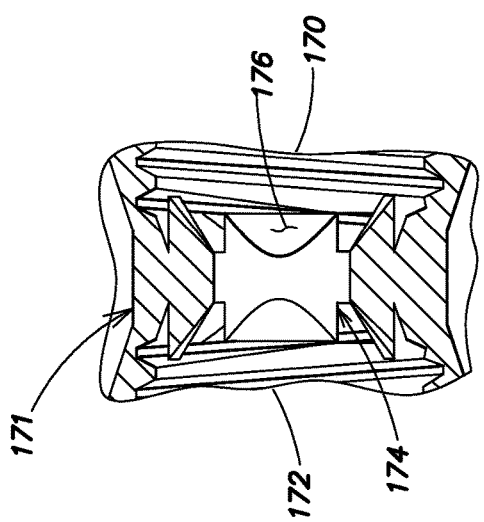
FIG. 20A illustrates a cross-sectional view of the connector that can engage the first and second syringe. There is a channel shown configured to engage the first and second syringes.

Referring to FIGS. 20A-20C, FIG. 20A illustrates a perspective view of an embodiment of the connector 171 that can engage the first and second syringe. The connector has openings 170 and 172 that each have a diameter that is the same or less than the diameter of the first and second syringe. In some embodiments, the connector 171 comprises a two way valve 174 that allows flow between first and second syringes and the channel in the connector. The connector provides a fluid seal and acts as a conduit between the two syringes. This is ideal for mixing. The connector can be plastic or metal or a combination thereof. In some embodiments, there is a fitting 176 to provide a further seal between first and second syringe when removably attached to the connector 171. FIG. 20B illustrates a cross-sectional view of the connector 171 having threading 180 and 178 that can engage the first and second syringe. The user takes first syringe with corresponding threading and engages threading 180 and takes second syringe with corresponding threading and engages threading 178 by turning the syringe or connector clockwise or counter clockwise until the device is assembled to provide an air-tight seal. Channel 184 acts as a conduit for mixing the material between syringes. FIG. 20C illustrates a side perspective view of the connector 171 having a channel 184 and fitting 176 that can engage the first syringe. The channel 184 can have a smaller diameter relative to the diameter of the syringe to create more pressure and a turbulent flow between first and second syringes and connector 171 to aid in mixing the components. Alternatively or in addition to the extension member, there can be a valve 174 disposed in the channel to change flow rates between first and second syringes and the connector. Projection 186 can be radially arrayed at discrete regions of the outer surface of the connector 171 to allow easier engagement of the connector by hand or machine.

In some embodiments, the device comprises one or more index markers disposed on the first syringe, second syringe, and/or connector to visually indicate alignment of the syringes with the connector and ensure that the chambers and channels are properly aligned for mixing of the bone material and to prevent leakage of liquid and bone material from the device.

In some embodiments, once the syringe containing the mixed bone material and liquid is removed from the connector, a needle can be connected to the syringe and the mixed bone material can be dispensed.

Methods of Treatment

Illustrative bone repair sites that can be treated with implantable compositions of the disclosure include, for instance, those resulting from injury, defects brought about during the course of surgery, infection, malignancy or developmental malformation. The composite bone graft compositions can be used in a wide variety of orthopedic, periodontal, neurosurgical and oral and maxillofacial surgical procedures including, but not limited to the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic enhancement; etc. Specific bones which can be repaired or replaced with the composite bone graft compositions or an implant comprising the compositions include, but are not limited to the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones.

In accordance with certain aspects of the disclosure, the bone graft compositions of the disclosure can be used as bone void fillers, or can be incorporated in, on or around a load bearing implants such as spinal implants, hip implants (e.g. in or around implant stems and/or behind acetabular cups), knee implants (e.g. in or around stems). In some embodiments, the implantable compositions of the disclosure can be incorporated in, on or around a load-bearing spinal implant device having a compressive strength of at least about 10000 N, such as a fusion cage, PEEK implants, dowel, or other device potentially having a pocket, chamber or other cavity for containing an osteoinductive composition, and used in a spinal fusion such as an interbody fusion. One illustrative such use is in conjunction with a load-bearing interbody spinal spacer to achieve interbody fusion. In these applications, the implantable composition can be placed in and/or around the spacer to facilitate the fusion.

Methods for preparing DBM are well known in the art as described, e.g. U.S. Pat. Nos. 5,314,476, 5,507,813, 5,073,373, and 5,405,390, each incorporated herein by reference. Methods for preparing ceramic powders of calcium phosphate and/or hydroxyapatite are described, e.g., in U.S. Pat. Nos. 4,202,055 and 4,713,076, each incorporated herein by reference.

In some embodiments, the method comprises obtaining the fibers by shaving, milling, or pressing the sheet or block under aseptic conditions. The shape of the fibers can be optimized for inducing new bone formation and handling properties via the network of fibers.

In a still further aspect, the present disclosure provides a method of accelerating bone formation at an implantable tissue regeneration scaffold. In a still further aspect, the present disclosure provides a method of regenerating bone in a patient in need thereof, comprising implanting the patient with the implantable composition.

In a still further aspect, the present disclosure provides a method of treating a bone defect caused by injury, disease, wounds, or surgery utilizing an implantable composition comprising a combination of fibers of demineralized bone matrix obtained from allograft bone, and fibers of non-allograft bone material, the fibers of non-allograft bone material comprising non-fibrous demineralized bone particles embedded within or disposed on the fibers of non-allograft bone material.

Kits

The present application also provides a medical kit for preparing the implantable compositions or the disclosure for treating a patient, the kit including at least a delivery system comprising a medical implant device as described above and a package enclosing the medical implant device in a sterile condition. Such kits can include a dried material containing the solid ingredients of the composition along with an aqueous medium or other biocompatible wetting liquid for combination with the dried material to form a malleable wetted material, or can include the formulated, wetted malleable implant material in a suitable container such as a syringe or vial (e.g. terminally sterilized), and/or another item such as a load-bearing implant (e.g., a spinal spacer), and/or a transfer device such as a syringe, and/or a therapeutic substance, for example an osteogenic substance such as a BMP. In one specific form, such a medical kit can include a dried material, such as a particulate or dried body, a BMP in lyophilized form (e.g., rhBMP-2), and an aqueous medium for reconstitution of the BMP to prepare an aqueous formulation that can then be added to the dried material in the process of preparing the composite bone graft composition of the disclosure.

In particular, in various embodiments, the device may comprise a bioerodible, a bioabsorbable, and/or a biodegradable biopolymer that may provide immediate release, or sustained release of the implantable composition. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG and/or PEG may be used as a plasticizer for PLGA, but other polymers/excipients may be used to achieve the same effect. In various embodiments, the implantable composition also comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

The coherent mass may have functional characteristics. Alternatively, other materials having functional characteristics may be incorporated into the coherent mass. Functional characteristics may include radiopacity, bacteriocidity, source for released materials, tackiness, etc. Such characteristics may be imparted substantially throughout the coherent mass or at only certain positions or portions of the coherent mass.

Suitable radiopaque materials include, for example, ceramics, mineralized bone, ceramics/calcium phosphates/calcium sulfates, metal particles, fibers, and iodinated polymer. Polymeric materials may be used to form the coherent mass and be made radiopaque by iodinating them. Other techniques for incorporating a biocompatible metal or metal salt into a polymer to increase radiopacity of the polymer may also be used. Suitable bacteriocidal materials may include, for example, trace metallic elements. In some embodiments, trace metallic elements may also encourage bone growth.

Functional material, such as radiopaque markers, may be provided at one or more locations on the coherent mass or may be provided substantially throughout the coherent mass. Thus, for example, in a cylindrical coherent mass, a radiopaque marker may be provided at a tip of the cylindrical coherent mass. Such marker may facilitate placement of the coherent mass. Radiopaque materials may be incorporated into the coherent mass and/or into the substance for delivery by the coherent mass. Further, radiopaque materials may be provided at only some locations on the coherent mass such that visualization of those locations provides indication of the orientation of the coherent mass in vivo.

The implantable composition of the disclosure can be used alone, as bone grafting materials, as scaffolds for bone tissue engineering for repair, augmentation and replacement of bone tissue or as carriers of growth factors, or carriers of genes.

It should be understood that the forgoing relates to exemplary embodiments of the disclosure and that modifications may be made without departing from the spirit and scope of the disclosure as set forth in the following claims.

The invention claimed is:

1. A method of implanting a bone material to a target tissue site, the method comprising contacting the bone material with a liquid, the bone material comprising a coherent mass of cartridge milled, lyophilized and demineralized bone fibers, the coherent mass of bone fibers having no binder disposed in or on the coherent mass; molding the coherent mass of the bone material into a cylinder to implant the bone material, wherein the cylinder has hydration channels on an exterior surface, the hydration channels extending along a longitudinal axis of the cylinder; and implanting the bone material at the target tissue site.

2. A method of implanting of claim 1, wherein the liquid comprises blood, water, saline or a combination thereof that is contacted with the bone material to form moldable bone material.

3. A method of implanting of claim 1, wherein the fibers have an aspect ratio of from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1.

4. A method of implanting of claim 1, wherein the coherent mass comprises a first end having a first diameter and a second end having a second diameter, the first diameter is wider than or the same size as the second diameter.

5. A method of implanting of claim 1, wherein the hydration channels have a rounded inner surface.

6. A method of implanting of claim 1, wherein the hydration channels have a straight inner surface.

7. A method of implanting a bone material to a target tissue site, the method comprising providing the bone material and contacting the bone material with a liquid, the bone material comprising a coherent mass of milled and demineralized bone fibers, the coherent mass of milled and demineralized bone fiber having no binder disposed in or on the coherent mass, wherein the coherent mass is shaped into a cylinder and the cylinder has hydration channels on an exterior surface of the coherent mass, the hydration channels extending along a longitudinal axis of the cylinder.

8. A method of implanting of claim 7, wherein the bone material is lyophilized.

9. A method of implanting of claim 8, wherein the coherent mass of milled and lyophilized demineralized bone fibers are cartridge milled fibers having a ribbon-like shape, increased surface area and a curled portion.

10. A method of implanting of claim 8, wherein the coherent mass of milled and lyophilized demineralized bone fibers comprise autograft or allograft bone.

11. A method of implanting of claim 7, wherein the milled and demineralized bone fibers are cartridge milled and have a ribbon-like shape with increased surface area compared to demineralized bone powder.

12. A method of implanting of claim 7, wherein the bone fibers have a diameter from about 100 μm to about 2 mm.

13. A method of implanting of claim 7, wherein the fibers have an aspect ratio of from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1.

14. A method of implanting of claim 7, wherein the liquid comprises blood, water, saline or a combination thereof.

15. A method of implanting of claim 7, wherein the liquid is mixed with the coherent mass of milled and demineralized bone fibers that are lyophilized without a binder to form moldable lyophilized demineralized bone fibers.

16. A method of implanting a bone material to a target tissue site, the method comprising contacting the bone material for hydration with a liquid, the bone material comprising a coherent mass of cartridge milled, lyophilized and demineralized bone fibers, the coherent mass of milled, lyophilized and demineralized bone fibers having no binder disposed in or on the coherent mass, wherein the coherent mass is shaped as a cylinder and the cylinder has hydration channels on an exterior surface, the hydration channels extending along a longitudinal axis of the cylinder.

17. A method of implanting of claim 16, wherein the coherent mass of cartridge milled and lyophilized demineralized bone fibers have a ribbon-like shape and increased surface area compared to demineralized bone powder.

18. A method of implanting of claim 17, wherein the coherent mass of cartridge milled and lyophilized demineralized bone fibers comprise autograft or allograft bone.

19. A method of implanting of claim 17, wherein the fibers have an aspect ratio of from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1.

20. A method of implanting of claim 17, wherein the liquid is mixed with the coherent mass of cartridge milled and demineralized bone fibers that are lyophilized without a binder to form moldable lyophilized demineralized bone fibers.

* * * * *